US008511888B2

(12) United States Patent
Nagai et al.

(10) Patent No.: US 8,511,888 B2
(45) Date of Patent: Aug. 20, 2013

(54) REAGENT PREPARING APPARATUS, SAMPLE PROCESSING APPARATUS AND REAGENT PREPARING METHOD

(75) Inventors: Takaaki Nagai, Kobe (JP); Masaharu Shibata, Kobe (JP); Kunio Ueno, Kakogawa (JP); Noriyuki Nakanishi, Kakogawa (JP)

(73) Assignee: Sysmex Corporation, Kobe (JP)

( * ) Notice: Subject to any disclaimer, the term of this patent is extended or adjusted under 35 U.S.C. 154(b) by 638 days.

(21) Appl. No.: 12/583,363

(22) Filed: Aug. 18, 2009

(65) Prior Publication Data

US 2010/0055772 A1 Mar. 4, 2010

(30) Foreign Application Priority Data

Aug. 26, 2008 (JP) ................................. 2008-216067

(51) Int. Cl.
*G05D 11/02* (2006.01)
(52) U.S. Cl.
USPC ................ 366/152.1; 366/152.2; 366/132; 366/131; 366/160.1; 366/182.2; 422/67; 422/68.1; 422/505; 422/105; 422/106; 422/110; 422/417
(58) Field of Classification Search
USPC .................. 422/41, 547, 559, 110, 404, 417, 422/62–68.1, 505, 215, 105–106; 436/50, 436/52, 43, 55, 54, 166, 179–180; 366/132, 366/131, 152.1, 152.2, 160.1, 160.2, 181.2, 366/181.3, 181.8, 182.1, 182.2, 182.3, 182.4, 366/189–192; 137/340
See application file for complete search history.

(56) References Cited

U.S. PATENT DOCUMENTS

| | | | | |
|---|---|---|---|---|
| 3,322,363 A * | 5/1967 | Davidson et al. | ............. | 242/552 |
| 5,697,702 A * | 12/1997 | Triassi et al. | ............... | 366/152.2 |
| 5,800,056 A * | 9/1998 | Suzuki et al. | ............... | 366/152.4 |
| 5,884,649 A * | 3/1999 | Proudman | ........................ | 137/7 |
| 5,887,975 A * | 3/1999 | Mordaunt et al. | ........... | 366/152.1 |
| 5,924,794 A * | 7/1999 | O'Dougherty et al. | ........ | 366/136 |
| 5,980,836 A * | 11/1999 | Moffett et al. | ................. | 422/129 |
| 6,314,996 B1 * | 11/2001 | Borglum et al. | ........... | 137/565.29 |
| 6,604,849 B2 * | 8/2003 | Lin et al. | ..................... | 366/154.2 |
| 7,946,751 B2 * | 5/2011 | Niermeyer et al. | ......... | 366/152.1 |
| 7,980,753 B2 * | 7/2011 | Urquhart et al. | .............. | 366/132 |
| 2003/0198125 A1 * | 10/2003 | Linsen et al. | .............. | 366/152.1 |
| 2004/0141409 A1 * | 7/2004 | Breithaupt | ................. | 366/152.2 |
| 2004/0216780 A1 * | 11/2004 | Hammonds et al. | ..... | 137/101.21 |
| 2010/0031825 A1 * | 2/2010 | Kemp | ............................. | 99/275 |

FOREIGN PATENT DOCUMENTS

JP 01-167660 7/1989

* cited by examiner

*Primary Examiner* — Brian R Gordon
(74) *Attorney, Agent, or Firm* — Brinks Hofer Gilson & Lione

(57) ABSTRACT

The present invention is to present a reagent preparing apparatus for preparing a reagent for processing a sample, by using a first liquid and a second liquid, comprising: a storage unit for storing liquid; and a constant amount liquid quantifying unit comprising a constant amount holding instrument which is used in common to hold a constant amount of the first liquid and to hold a constant amount of the second liquid, the constant amount liquid quantifying unit performing an operation of transferring the constant amount of the first liquid to the storage unit and performing an operation of transferring the constant amount of the second liquid to the storage unit.

19 Claims, 16 Drawing Sheets

# REAGENT PREPARING APPARATUS, SAMPLE PROCESSING APPARATUS AND REAGENT PREPARING METHOD

RELATED APPLICATIONS

This application claims priority under 35 U.S.C. §119 to Japanese Patent Application No. 2008-216067 filed Aug. 26, 2008, the entire content of which is hereby incorporated by reference.

FIELD OF THE INVENTION

The present invention relates to a reagent preparing apparatus for preparing a reagent for processing a sample, a reagent preparing method, and a sample processing apparatus for processing a sample by using the prepared reagent.

BACKGROUND

A reagent preparing apparatus for preparing a reagent by diluting an undiluted solution of the reagent by using a dilution liquid is conventionally known.

For instance, Japanese Laid-Open Patent Publication No. H1-167660 discloses a reagent preparing apparatus including a liquid amount measurement tube for holding a predetermined amount of concentrated solution, and a liquid amount measurement tank for holding a predetermined amount of pure water. The reagent preparing apparatus is configured to prepare the reagent by mixing the concentrated solution supplied from the liquid amount measurement tube and the pure water supplied from the liquid amount measurement tank.

U.S. Pat. No. 5,800,056 discloses a reagent preparing apparatus including a reagent tank for holding a predetermined amount of high concentration reagent, a pure water tank for holding a predetermined amount of pure water, a reagent preparing tank, and a pump for supplying pure water to the reagent preparing tank by a small amount at a time. The reagent preparing apparatus supplies the high concentration reagent from the reagent tank to the reagent preparing tank, and supplies the pure water from the pure water tank to the reagent preparing tank by an amount less than the amount necessary for diluting the high concentration reagent to the desired concentration. Thereafter, the reagent preparing apparatus supplies pure water by the pump to the reagent preparing tank by a small amount at a time to approach the reagent in the reagent preparing tank to the desired concentration. The high concentration reagent thus can be diluted to the desired concentration at satisfactory accuracy.

However, in the reagent preparing apparatus described in Japanese Laid-Open Patent Publication No. H1-167660, since the concentrated solution is supplied from the liquid amount measurement tube and the pure water is supplied from the liquid amount measurement tank different from the liquid amount measurement tube, the concentrated solution becomes difficult to be diluted to the desired concentration at satisfactory accuracy due to the liquid amount measurement error caused by the assembly error and the like which occur in the tube and the tank.

In the reagent preparing apparatus described in U.S. Pat. No. 5,800,056, the reagent approaches the desired concentration by supplying the pure water from the pump to the reagent preparing tank by a small amount at a time, and thus the high concentration reagent can be diluted to the desired concentration at satisfactory accuracy. However, the preparing operation of the reagent becomes complicating, because the pure water needs to be repeatedly and continuously supplied from the pump to the reagent preparing tank by a small amount at a time until the reagent in the reagent preparing tank reaches the desired concentration. A reagent preparing apparatus capable of preparing the desired reagent at satisfactory accuracy with a simple operation is desired.

SUMMARY

A first aspect of the present invention is a reagent preparing apparatus for preparing a reagent for processing a sample, by using a first liquid and a second liquid, comprising: a storage unit for storing liquid; and a constant amount liquid quantifying unit comprising a constant amount holding instrument which is used in common to hold a constant amount of the first liquid and to hold a constant amount of the second liquid, the constant amount liquid quantifying unit performing an operation of transferring the constant amount of the first liquid to the storage unit and performing an operation of transferring the constant amount of the second liquid to the storage unit.

A second aspect of the present invention is a sample processing apparatus comprising: a storage unit for storing liquid; a constant amount liquid quantifying unit comprising a constant amount holding instrument which is used in common to hold a constant amount of the first liquid and to hold a constant amount of the second liquid, the constant amount liquid quantifying unit performing an operation of transferring the constant amount of the first liquid to the storage unit and performing an operation of transferring the constant amount of the second liquid to the storage unit; and a sample processing unit for processing a sample by using a reagent prepared from the first liquid and the second liquid stored in the storage unit.

A third aspect of the present invention is a reagent preparing method for preparing a reagent for processing a sample, by using a first liquid and a second liquid, comprising steps of: holding a constant amount of the first liquid by using a constant amount holding instrument which is used in common to hold the constant amount of the first liquid and to hold a constant amount of the second liquid; transferring the constant amount of the first liquid to the storage unit; holding the constant amount of the second liquid by using the constant amount holding instrument; transferring the constant amount of the second liquid to the storage unit; and mixing the first liquid and the second liquid stored in the storage unit.

DETAILED DESCRIPTION OF THE EMBODIMENT

An embodiment of the present invention will be described below based on the drawings.

First, a configuration of a reagent preparing apparatus 4 according to a first embodiment of the present invention will be described with reference to FIGS. 1 to 14. In the present embodiment, a case of using the reagent preparing apparatus 4 according to the present invention as part of a blood analyzer 1 for conducting blood test will be described.

Figure 1:
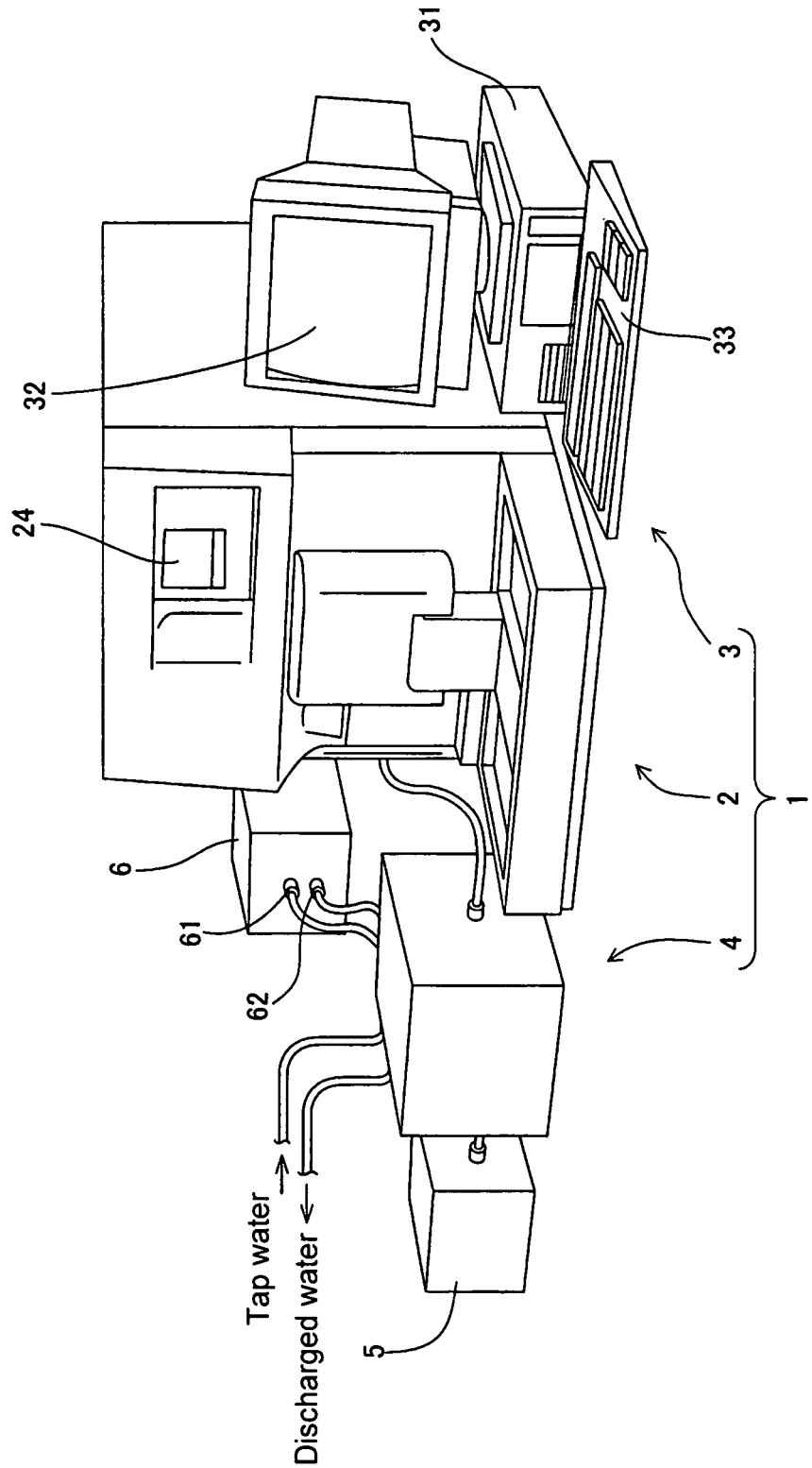
FIG. 1 is a perspective view showing a usage state of a reagent preparing apparatus according to one embodiment of the present invention.

As shown in FIG. 1, the blood analyzer 1 is configured by a measurement section 2 having a function of measuring blood, a data processing section 3 for analyzing the measurement data output from the measurement section 2 and obtaining the analysis result, and the reagent preparing apparatus 4 according to one embodiment of the present invention for preparing the reagent used in the processing of a sample. The measurement section 2 is configured to measure the white blood cells, the reticulocytes, and the platelets in the blood through the flow cytometry method. The flow cytometry method is a measurement method of particles (blood cells) of detecting the forward scattered light, the lateral scattered light, and the lateral fluorescence emitted by the particles (blood cells) in the measurement sample by forming a specimen flow containing the measurement sample and irradiating laser light on the specimen flow.

Figure 2:
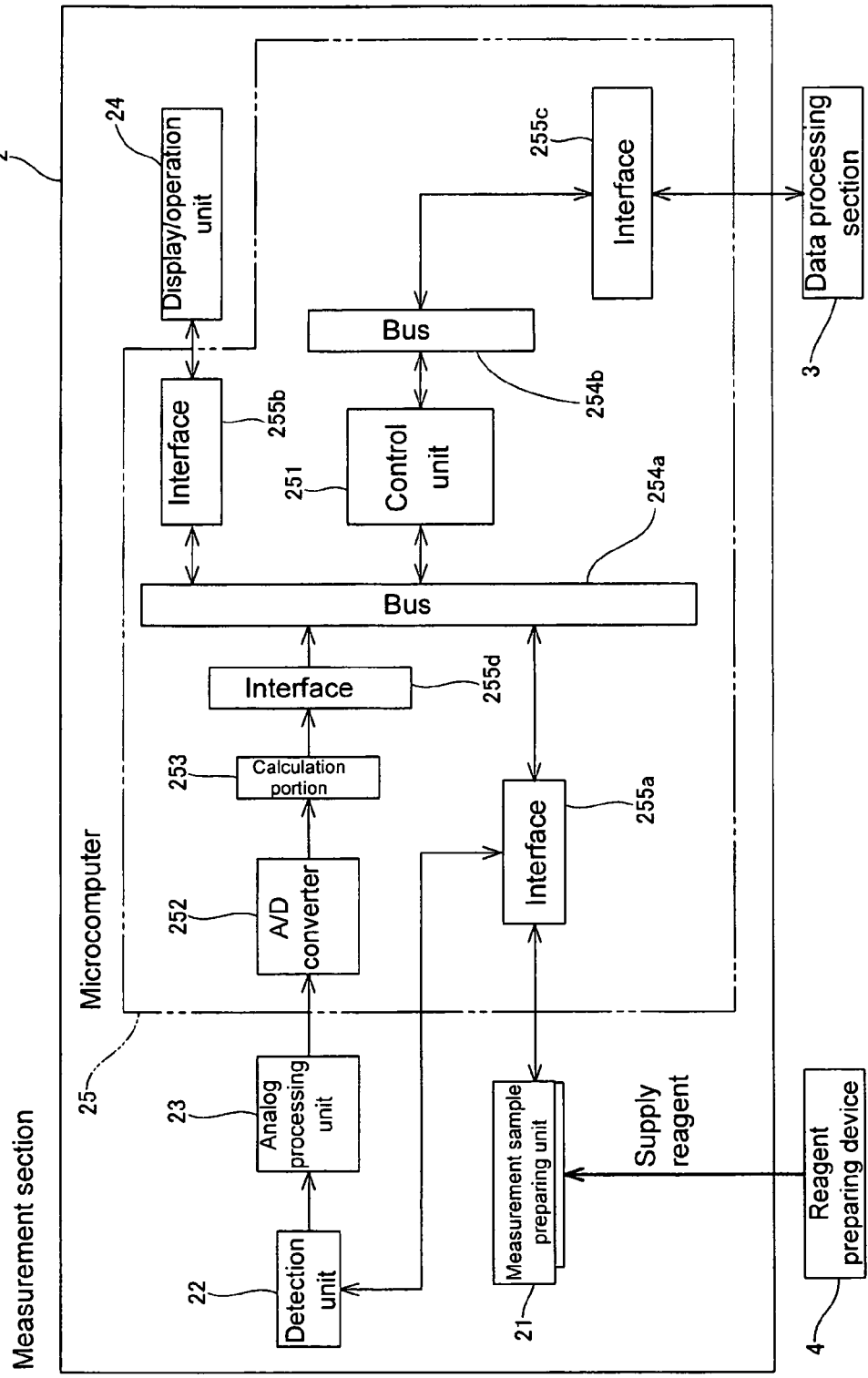
FIG. 2 is a block diagram showing a configuration of a blood analyzer including the reagent preparing apparatus according to one embodiment shown in FIG. 1.

As shown in FIG. 2, the measurement section 2 includes a measurement sample preparing unit 21, a detection unit 22 for measuring the measurement sample, an analog processing unit 23 with respect to the output of the detection unit 22, a display/operation unit 24, and a microcomputer 25 for controlling the measurement section 2.

Figure 3:
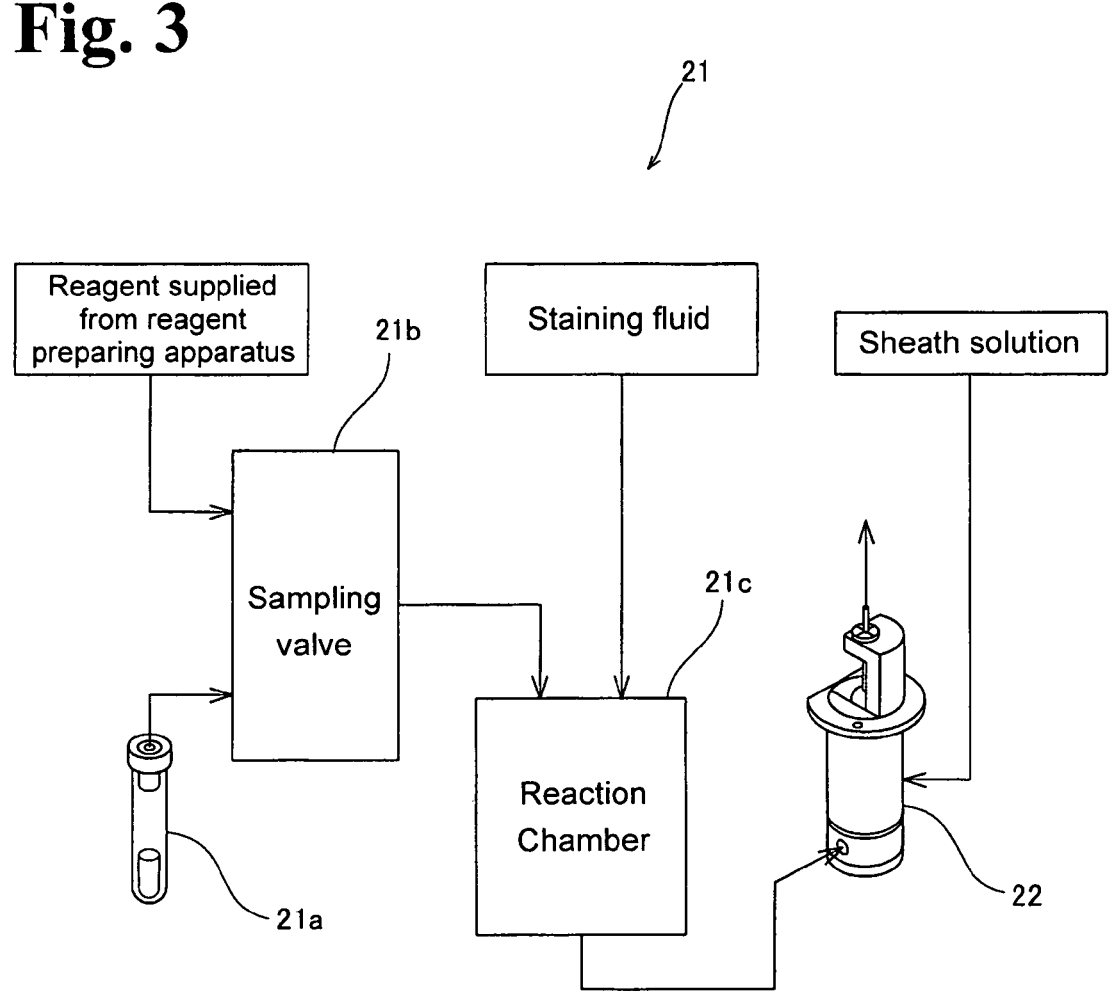
FIG. 3 is a view describing a specimen preparing unit of the blood analyzer including the reagent preparing apparatus according to one embodiment shown in FIG. 1.

The measurement sample preparing unit 21 is arranged to prepare the white blood cell measurement sample, the reticulocyte measurement sample, and the platelet measurement sample. As shown in FIG. 3, the measurement sample preparing unit 21 includes a blood collecting tube 21a filled with a predetermined amount of blood, a sampling valve 21b from which the blood is aspirated, and a reaction chamber 21c. The blood collecting tube 21a is replaceable, and is configured such that the blood can be replaced.

The sampling valve 21b has a function of quantifying the blood of the blood collecting tube 21a aspirated by an aspiration pipette (not shown) by a predetermined amount. The sampling valve 21b is configured such that a predetermined reagent can be mixed to the aspirated blood. That is, the sampling valve 21b is configured to generate a diluted specimen in which a predetermined amount of reagent is supplied from the reagent preparing apparatus 4 to a predetermined amount of blood.

The reaction chamber 21c is configured to further mix a predetermined staining fluid to the diluted specimen supplied from the sampling valve 21b and react the same for a predetermined time. The measurement sample preparing unit 21 has a function of preparing the white blood cell measurement sample in which the white blood cells are stained and the red blood cells are hemolyzed. The measurement sample preparing unit 21 has a function of preparing the reticulocyte measurement sample in which the reticulocyte is stained and preparing the platelet measurement sample in which the platelet is stained.

The measurement sample preparing unit 21 is configured to supply the white blood cell measurement sample from the measurement sample preparing unit 21 to a sheath flow cell 22c (see FIG. 4), to be hereinafter described, with the sheath solution in time of white blood cell classification measurement (hereinafter described as "DIFF measurement") mode. The measurement sample preparing unit 21 is configured to supply the reticulocyte measurement sample from the measurement sample preparing unit 21 to the sheath flow cell 22c with the sheath solution in time of reticulocyte measurement (hereinafter described as "RET measurement") mode. The measurement sample preparing unit 21 is configured to supply the platelet measurement sample from the measurement sample preparing unit 21 to the sheath flow cell 22c with the sheath solution in time of platelet measurement (hereinafter described as "PLT measurement") mode.

Figure 4:
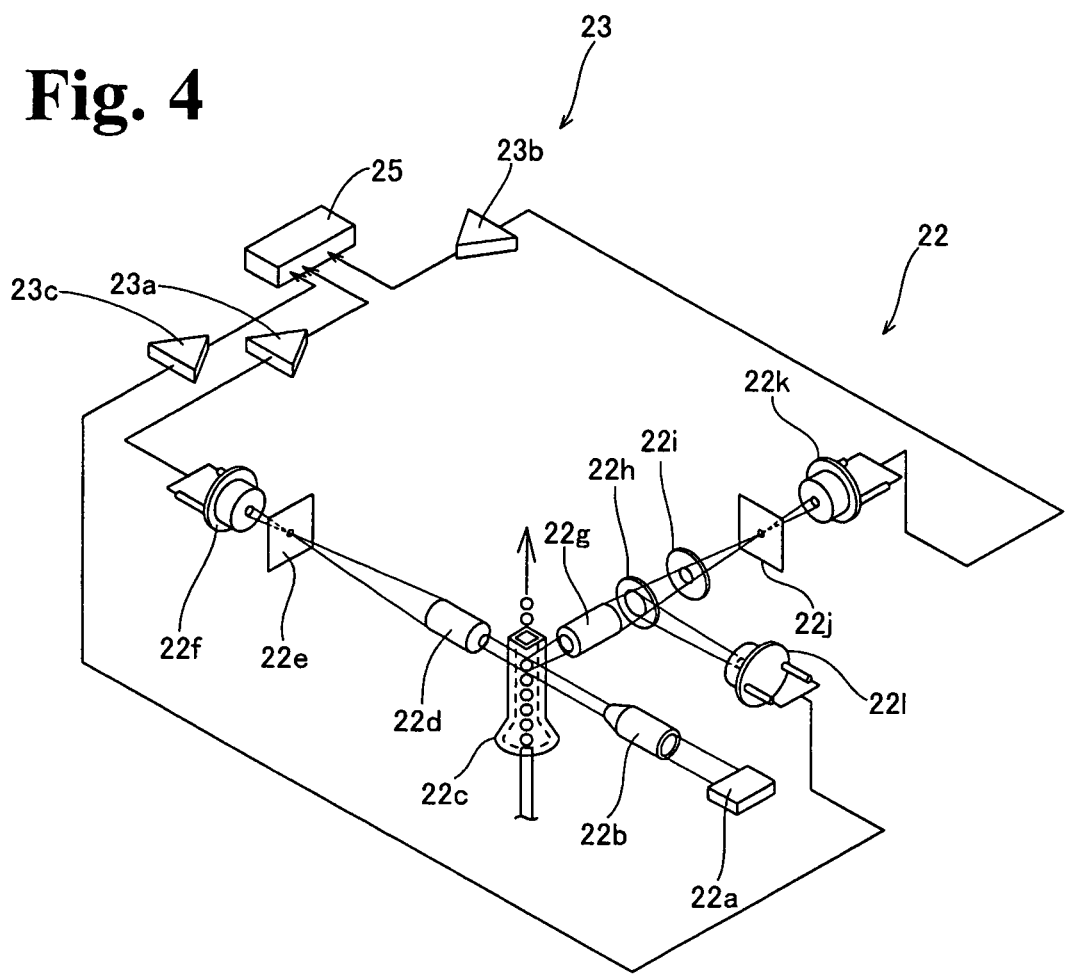
FIG. 4 is a schematic view showing a detection unit of the blood analyzer including the reagent preparing apparatus according to one embodiment shown in FIG. 1.

As shown in FIG. 4, the detection unit 22 includes a light emitting portion 22a for emitting the laser light, an irradiation lens unit 22b, a sheath flow cell 22c irradiated with the laser light, a light collecting lens 22d, a pin hole 22e, and a PD (photodiode) 22f arranged on an extended line in a direction the laser light emitted from the light emitting portion 22a advances, a light collecting lens 22g, a dichroic mirror 22h, an optical filter 22i, a pin hole 22j, and an APD (avalanche photodiode) 22k arranged in a direction intersecting the direction the laser light emitted from the light emitting portion 22a advances, and a PD 22l arranged at the side of the dichroic mirror 22h.

The light emitting portion 22a is arranged to emit light to the specimen flow including the measurement sample passing through the interior of the sheath flow cell 22c. The irradiation lens unit 22b is arranged to convert the light emitted from the light emitting portion 22a to parallel light. The PD 22f is arranged to receive the forward scattered light emitted from the sheath flow cell 22c. The information related to the size of the particle (blood cell) in the measurement sample can be obtained from the forward scattered light emitted from the sheath flow cell 22c.

The dichroic mirror 22h is arranged to separate the lateral scattered light and the lateral fluorescence emitted from the sheath flow cell 22c. Specifically, the dichroic mirror 22h is arranged to enter the lateral scattered light emitted from the sheath flow cell 22c to the PD 22l and to enter the lateral fluorescence emitted from the sheath flow cell 22c to the APD 22k. The PD 22l is arranged to receive the lateral scattered light. The internal information such as the size of the nuclei of the particle (blood cell) in the measurement sample can be obtained from the lateral scattered light emitted from the sheath flow cell 22c. The APD 22k is arranged to receive the lateral fluorescence. The information related to the staining degree of the particle (blood cell) in the measurement sample can be obtained from the lateral fluorescence emitted from the sheath flow cell 22c. The PD 22f, 22l and the APD 22k respectively function to convert the received light signal to an electrical signal.

As shown in FIG. 4, the analog processing unit 23 includes amplifiers 23a, 23b, and 23c. Each amplifier 23a, 23b, and 23c is arranged to perform amplification and waveform processing on the electric signal output from the PD 22f, 22l, and APD 22k.

As shown in FIG. 2, the microcomputer 25 includes a control unit 251 including a control processor and a memory for operating the control processor, an A/D converter 252 for converting a signal output from the analog processing unit 23 to a digital signal, and a calculation portion 253 for performing a predetermined process on the digital signal output from the A/D converter 252.

The control unit 251 has a function of controlling the measurement sample preparing unit 21 and the detection unit 22 by way of a bus 254a and an interface 255a. The control unit 251 is also connected to the display/operation unit 24 by way of the bus 254a and the interface 255b, and connected to the data processing section 3 by way of the bus 254b and the interface 255c. The calculation portion 253 has a function of outputting the calculation result to the control unit 251 via the interface 255d and the bus 254a. The control unit 251 also has a function of transmitting the calculation result (measurement data) to the data processing section 3.

Figure 5:
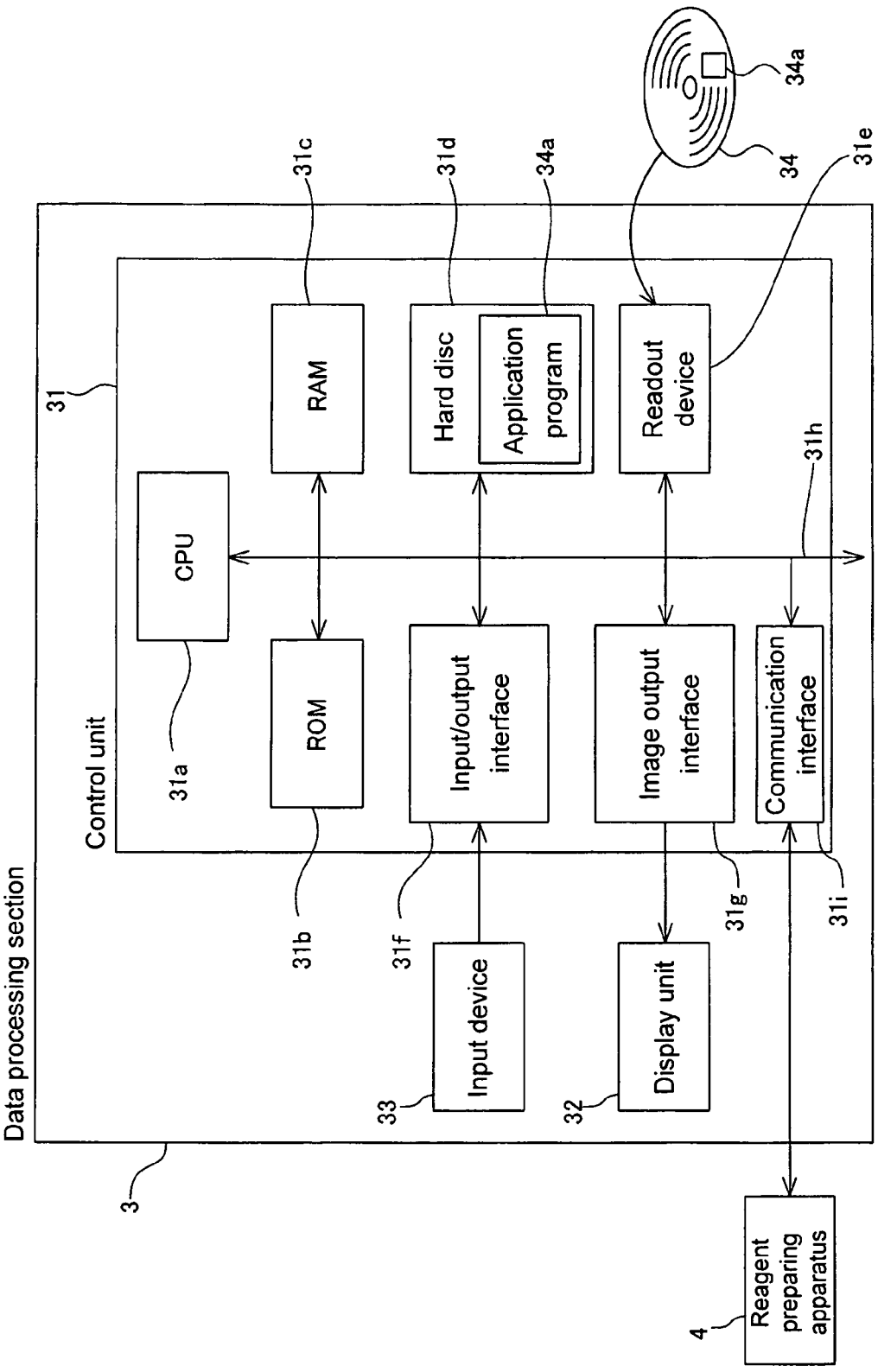
FIG. 5 is a block diagram showing a configuration of a data processing section of the blood analyzer including the reagent preparing apparatus according to one embodiment shown in FIG. 1.

As shown in FIG. 1, the data processing section 3 includes a personal computer (PC), and the like, and has a function of analyzing the measurement data of the measurement section 2 and displaying the analysis result. The data processing section 3 includes a control unit 31, a display unit 32, and an input device 33, as shown in FIG. 5.

The control unit 31 has a function of transmitting a measurement start signal including measurement mode information and a shutdown signal to the measurement section 2. As shown in FIG. 5, the control unit 31 is configured by a CPU 31a, a ROM 31b, a RAM 31c, a hard disc 31d, a readout device 31e, an input/output interface 31f, an image output interface 31g, and a communication interface 31i. The CPU 31a, the ROM 31b, the RAM 31c, the hard disc 31d, the readout device 31e, the input/output interface 31f, the image output interface 31g, and the communication interface 31i are connected to each other by a bus 31h.

The CPU 31a is arranged to execute the computer program stored in the ROM 31b and the computer program loaded to the RAM 31c. The ROM 31b is configured by mask ROM, PRM, EPROM, EEPROM, and the like, and stores the computer program executed by the CPU 31a, the data used when executing the computer program, and the like.

The RAM 31c is configured by SRAM, DRAM, or the like. The RAM 31c is used to read out the computer program stored in the ROM 31b and the hard disc 31d. The RAM 31c is used as a work region of the CPU 31a when executing such computer programs.

The hard disc 31d stores various computer programs to be executed by the CPU 31a, and the data used for the execution of the computer program such as an operating system and an application program. The application program 34a to be hereinafter described is also installed in the hard disc 31d.

The readout device 31e is configured by flexible disc drive, CD-ROM drive, DVD-ROM, or the like. The readout device 31e can read out computer program or data stored in a portable storage medium 34, and the like. The portable storage medium 34 stores the application program 34a for causing the computer to realize a predetermined function. The computer serving as the data processing section 3 reads out the application program 34a from the portable recording medium 34, and installs the application program 34a in the hard disc 31d.

The application program 34a is not limited to being provided by the portable storage medium 34, and may be provided through an electrical communication line from an external device communicably connected to the data processing section 3 by the electrical communication line (wired or wireless). For instance, the application program 34a may be stored in a hard disc of a server computer on the Internet, and the data processing section 3 may access the server computer and download the application program 34a from the server computer and store the same in the hard disc 31d.

The hard disc 31d is installed with an operating system providing a graphical user interface environment such as Windows (registered trademark) manufactured and sold by US Microsoft Co. In the following description, the application program 34a according to the present embodiment operates on the operating system.

The input/output interface 31f is configured by serial interface such as USB, IEEE1394, RS-232C; parallel interface such as SCSI, IDE, IEEE1284; analog interface including D/A converter, A/D converter and the like. The input/output interface 31f is connected with an input device 33 such as a keyboard and a mouse, and the user can input data to the data processing section 3 by using the input device 33. The input device 33 has a function of accepting the measurement mode.

The image output interface 31g is connected to the display unit 32 configured by LCD, CRT, or the like, and outputs a video signal corresponding to the image data provided from the CPU 31a to the display unit 32. The display unit 32 displays an image (screen) according to the input video signal.

In the present embodiment, the reagent preparing apparatus 4 is arranged to prepare a reagent used in the measurement sample preparing unit 21 of the measurement section 2. Specifically, the reagent preparing apparatus 4 is configured to prepare a diluted solution (hereinafter referred to as "reagent") used in blood analysis by diluting the salt solution (hereinafter referred to as "high concentration reagent") of high salinity, or the undiluted solution of the diluted solution, by using the RO water produced from tap water. The RO water is the water removed with impurities by being passed through the RO (Reverse Osmosis) film (reverse osmosis membrane).

Figure 6:
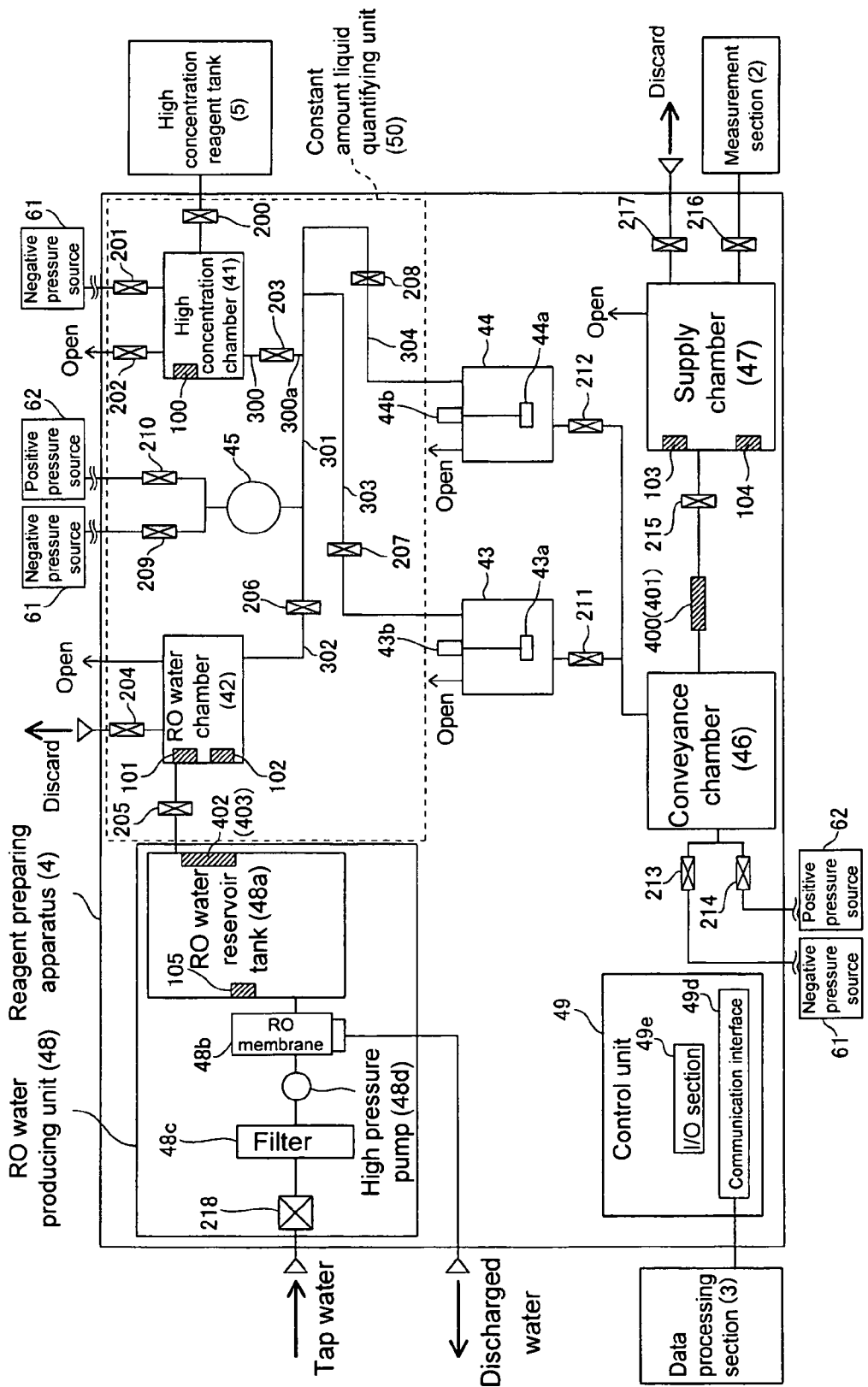
FIG. 6 is a block diagram showing the configuration of the reagent preparing apparatus according to one embodiment shown in FIG. 1.

As shown in FIG. 6, the reagent preparing apparatus 4 includes a high concentration reagent chamber 41, a RO water chamber 42, two mixing chambers 43 and 44, a diaphragm pump 45, a conveyance chamber 46, a supply chamber 47, a RO water producing unit 48, and a control unit 49 for controlling the operation of each unit of the reagent preparing apparatus 4. Furthermore, the reagent preparing apparatus 4 includes an air pressure unit 6 installed exterior to the housing (see FIG. 1), and is configured to convey each liquid in the apparatus by using negative pressure and positive pressure supplied from the air pressure unit 6. The air pressure unit 6 includes a negative pressure source 61 for supplying negative pressure and a positive pressure source 62 for supplying positive pressure to the reagent preparing apparatus 4.

The high concentration reagent chamber 41 is configured to supply the high concentration reagent from the high concentration reagent tank 5. The high concentration reagent chamber 41 is arranged with a float switch 100 for detecting that a predetermined amount of high concentration reagent is stored in the chamber. The high concentration reagent chamber 41 is connected to the high concentration reagent tank 5 by way of an electromagnetic valve 200 and connected to the negative pressure source 61 of the air pressure unit 6 by way of an electromagnetic valve 201. The high concentration reagent chamber 41 is configured to open or close with respect to atmosphere by the opening and closing of an electromagnetic valve 202. The high concentration reagent chamber 41 is connected to a flow path 301 for conveying the liquid from the diaphragm pump 45 to the mixing chambers 43 and 44 by a flow path 300. An electromagnetic valve 203 is arranged on the flow path 300, which electromagnetic valve 203 is arranged in the vicinity of the flow path 301. Specifically, the length of a flow path 300a between the electromagnetic valve 203 and the flow path 301 is set to a small length of about 15 mm. The flow path 300 (300a) connected to the high concentration reagent chamber 41 has an inner diameter of about 1.8 mm, and the flow path 301 has an inner diameter of about 4.0 mm.

The RO water chamber 42 is configured to be supplied with the RO water for diluting the high concentration reagent from the RO water producing unit 48. The RO water chamber 42 is arranged with float switches 101 and 102 for detecting that the RO water stored in the chamber has reached the upper limit amount and the lower limit amount, respectively. The RO water chamber 42 is configured to be able to discard the RO water in the chamber by opening the electromagnetic valve 204. The RO water chamber 42 is configured to be in a state constantly opened to atmosphere. The RO water chamber 42 is connected to a RO water reservoir tank 48a of the RO water producing unit 48, to be hereinafter described, by way of an electromagnetic valve 205. The RO water chamber 42 is connected to the diaphragm pump 45 by the flow path 302 by way of an electromagnetic valve 206.

The mixing chambers 43 and 44 store the high concentration reagent and the RO water, and are arranged to prepare the reagent used in blood analysis. The mixing chamber 43 is arranged with a stirring unit 43a for mixing and stirring the stored high concentration reagent and the RO water, where the stirring unit 43a is driven by a motor 43b. The mixing chamber 43 is configured to be in a state constantly opened to atmosphere. The mixing chamber 43 is connected to the flow path 301 by the flow path 303 by way of an electromagnetic valve 207. Similar to the flow path 301, the flow path 303 has an inner diameter of about 4 mm.

The mixing chamber 44 is configured similar to the mixing chamber 43, where a stirring unit 44a and a motor 44b correspond to the stirring unit 43a and the motor 43b. The electromagnetic valve 208 and the flow path 304 respectively correspond to the electromagnetic valve 207 and the flow path 303. The liquid (RO water and high concentration region) conveyed through the flow path 301 can be conveyed to the mixing chamber 43 by opening the electromagnetic valve 207 with the electromagnetic valve 208 closed. The liquid (RO water and high concentration region) conveyed through the flow path 301 can be conveyed to the mixing chamber 44 by opening the electromagnetic valve 208 with the electromagnetic valve 207 closed. In other words, the electromagnetic valves 207 and 208 are respectively configured to function as a flow path switching unit of the flow paths 303 and 304.

The diaphragm pump 45 has a function of holding a predetermined amount of the high concentration reagent and the RO water by about 6.0 ml (predetermined amount) in a single operation for holding liquid. The diaphragm pump 45 is connected to the negative pressure source 61 by way of the electromagnetic valve 209 and is connected to the positive pressure source 62 by way of the electromagnetic valve 210.

Figure 7:
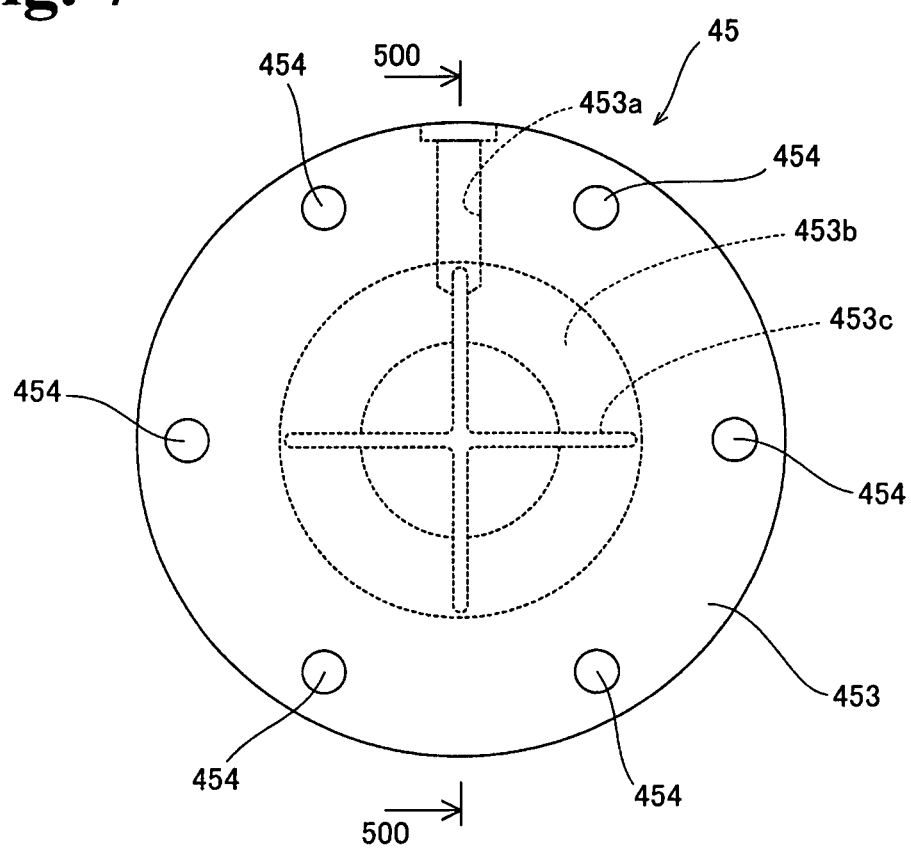
FIG. 7 is a plan view showing a diaphragm pump of the reagent preparing apparatus according to one embodiment shown in FIG. 1.
Figure 8:
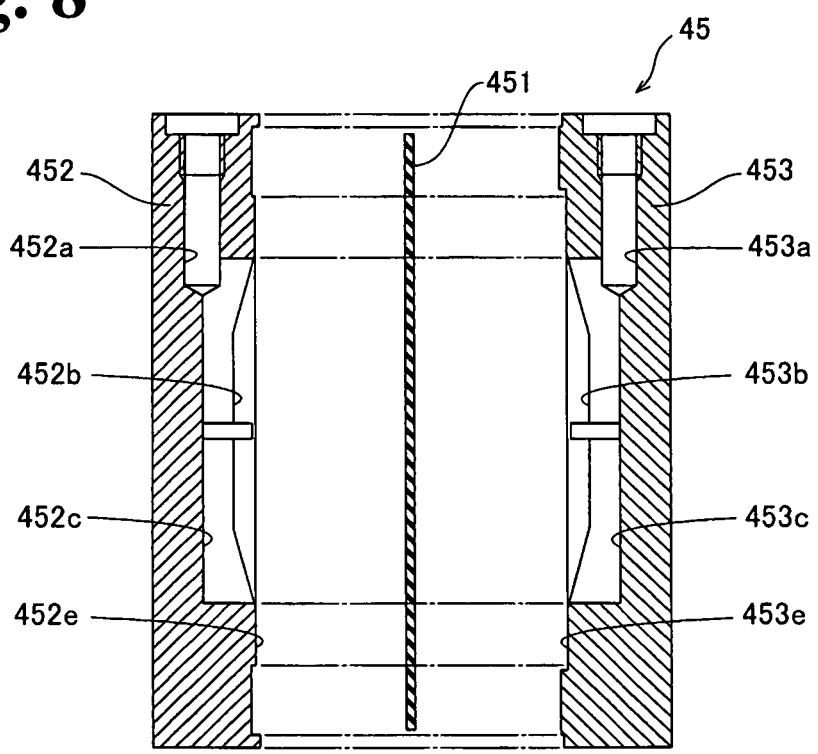
FIG. 8 is an exploded view at a cross-section taken along line 500-500 of FIG. 7.
Figure 9:
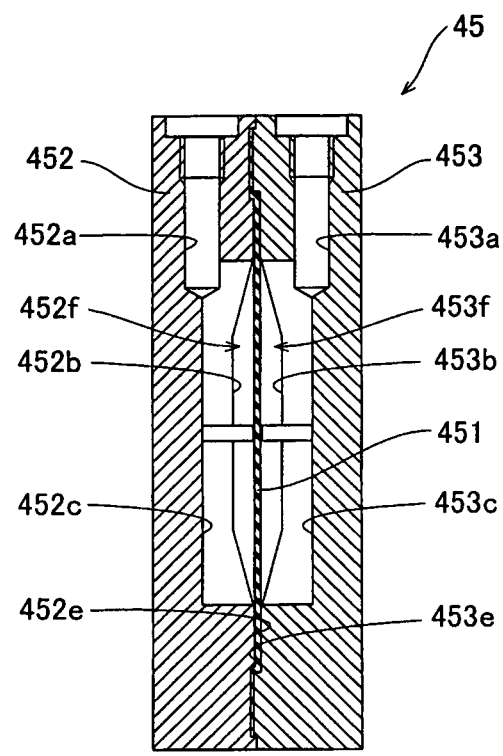
FIG. 9 is a cross-sectional view taken along line 500-500 of FIG. 7.

As shown in FIG. 7, the diaphragm pump 45 has a circular shape in plan view. As shown in FIGS. 8 and 9, the diaphragm pump 45 includes a film body 451 made of rubber material such as EPDM, and a pair of case pieces 452 and 453 configured to sandwich the film body 451 from both sides.

Figure 10:
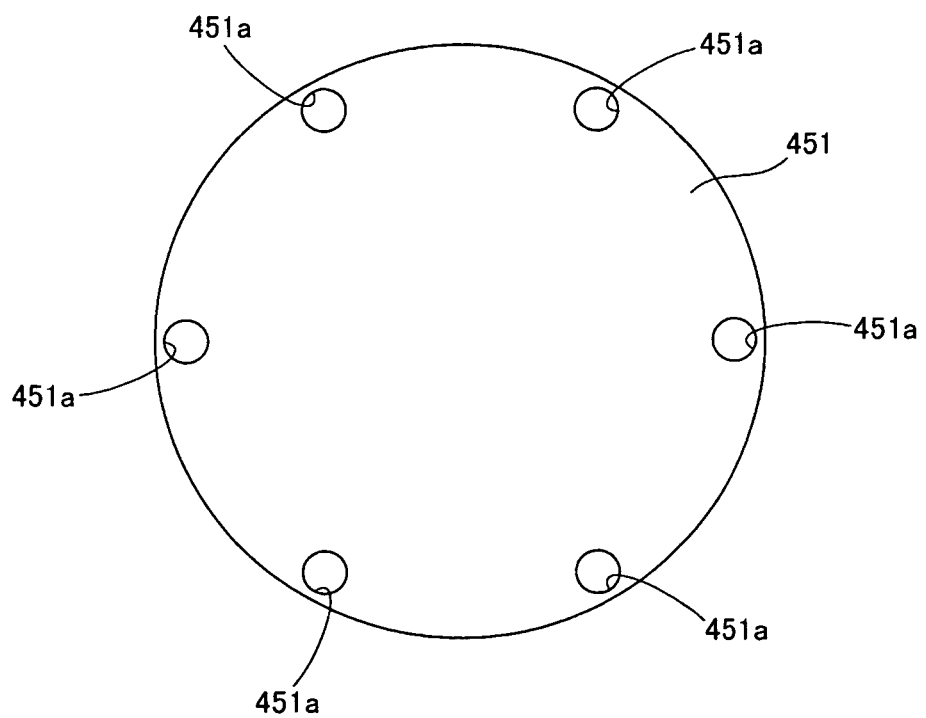
FIG. 10 is a plan view showing a film body of a diaphragm pump of the reagent preparing apparatus according to one embodiment shown in FIG. 1.

As shown in FIG. 10, the film body 451 is formed to a flat plate shape having a circular shape in plan view, and includes six screw holes 451a for passing the screw 454. As shown in FIGS. 8 and 9, the film body 451 is configured to be sandwiched from both sides by the case pieces 452 and 453.

Figure 11:
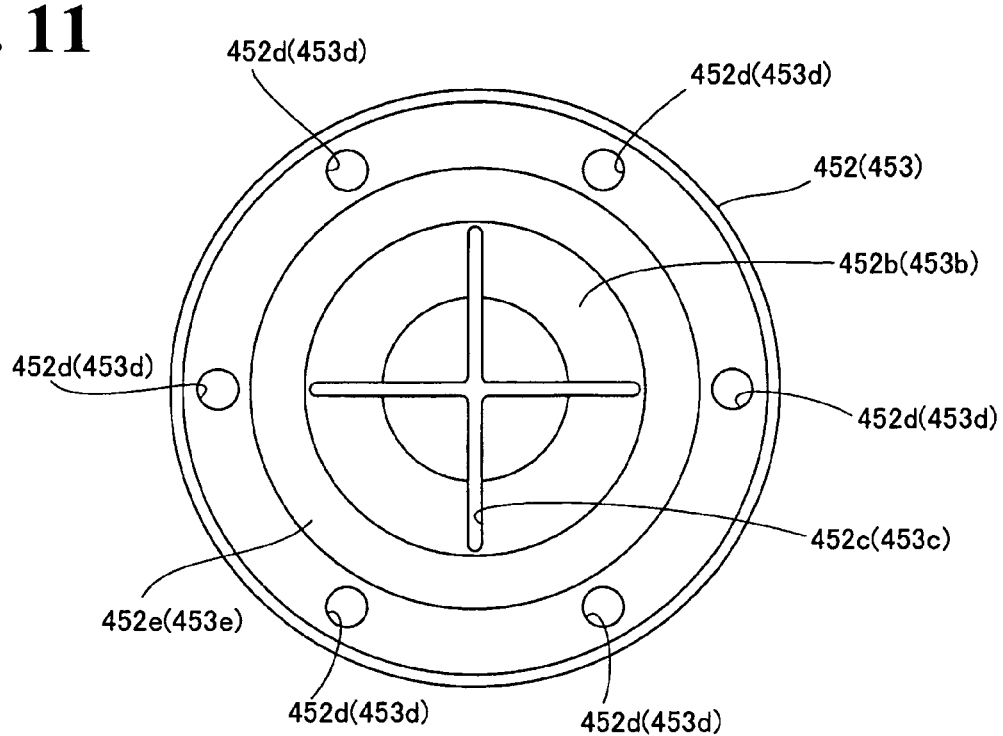
FIG. 11 is a plan view describing an internal structure of the diaphragm pump of the reagent preparing apparatus according to one embodiment shown in FIG. 1.

As shown in FIGS. 8, 9, and 11, the case piece 452 includes a flow port portion 452a (see FIGS. 8 and 9), an inner wall 452b formed to a circular truncated cone shape, a cross-shaped groove 452c arranged at substantially the middle of the inner wall 452b when seen in plan view, six screw holes 452d (see FIG. 11), and a ring-shaped sandwiching portion 452e formed to surround the inner wall 452b when seen in plan view. As shown in FIGS. 8, 9, and 11, the case piece 453 is configured similar to the case piece 452, where a flow portion 453a (see FIGS. 8 and 9), an inner wall 453b, a groove 453c, a screw hole 453d (see FIG. 11), and a sandwiching portion 453e correspond to the flow portion 452a, the inner wall 452b, the groove 452c, the screw hole 452d, and the sandwiching portion 452e.

As shown in FIG. 9, the case pieces 452 and 453 are joined to each other with six screws 454 (see FIG. 7) while sandwiching the film body 451 with the sandwiching portions 452e and 453e. A chamber portion 452f surrounded by the inner wall 452b and the film body 451, and a chamber portion 453f surrounded by the inner wall 453b and the film body 451 are thereby formed. The flow port portion 452a and the chamber portion 452f are spatially connected to each other by way of the groove 452c, and the flow port portion 453a and the chamber portion 453f are spatially connected to each other by way of the groove 453c. The chamber portions 452f and 453f are spatially spaced apart from each other by the film body 451.

Figure 12:
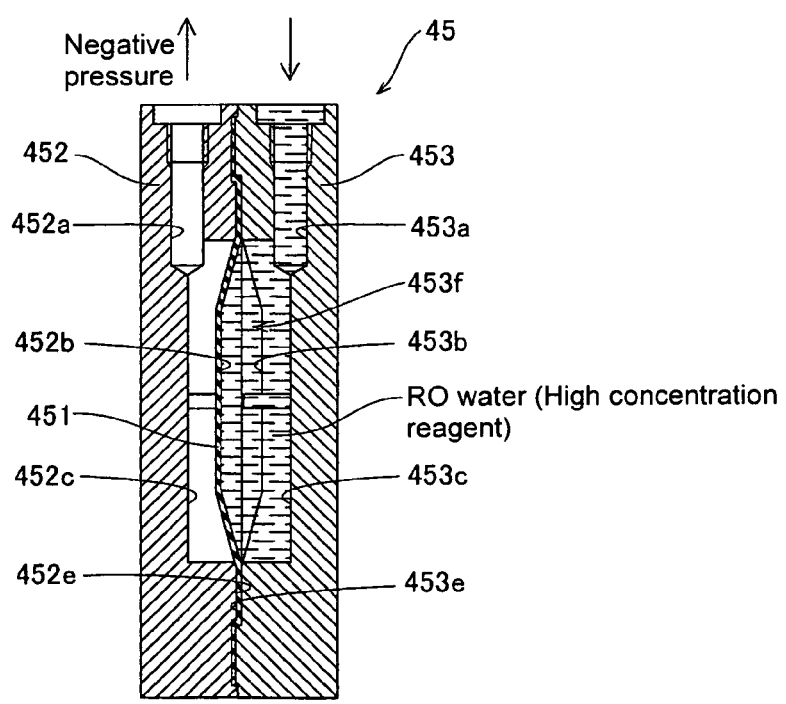
FIG. 12 is a cross-sectional view describing the configuration of the diaphragm pump of the reagent preparing apparatus according to one embodiment shown in FIG. 1.
Figure 13:
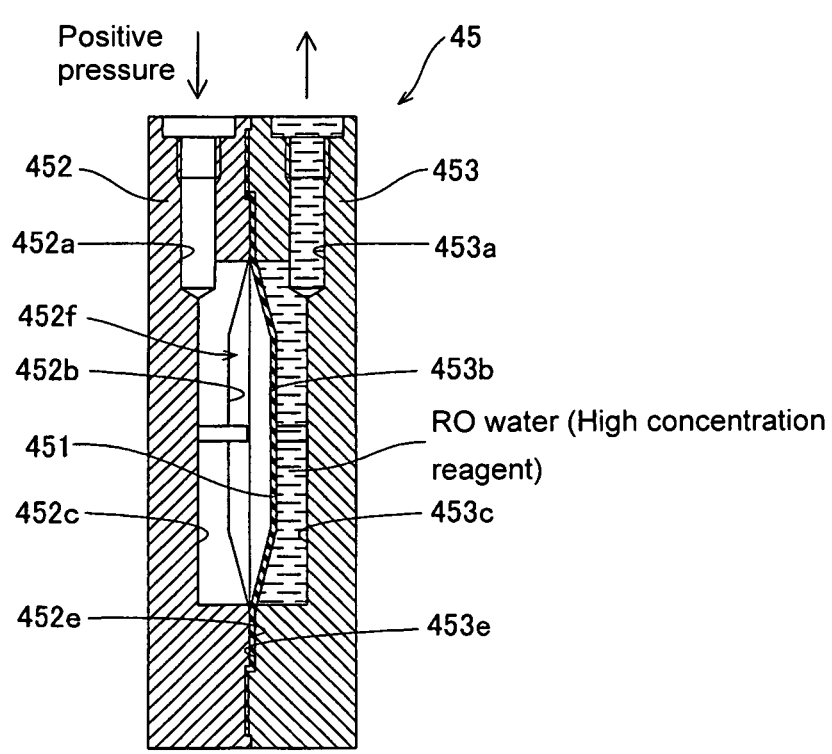
FIG. 13 is a cross-sectional view describing the configuration of the diaphragm pump of the reagent preparing apparatus according to one embodiment shown in FIG. 1.

The flow port portion 452a is connected to the negative pressure source 61 and the positive pressure source 62. The flow port portion 453a is connected to the flow path 302 connected to the RO water chamber 42 and the flow path 301 for conveying the liquid to the mixing chamber 43 (44). The diaphragm pump 45 is configured such that the film body 451 is closely attached to the inner wall 452b, as shown in FIG. 12, when the negative pressure is supplied to the chamber portion 452f by the negative pressure source 61 connected to the flow port portion 452a. The volume of the chamber portion 453f partitioned by the film body 451 thereby enlarges, and the liquid (RO water, high concentration reagent, or mixed solution of RO water and high concentration reagent) flows into the chamber portion 453f through the flow port portion 453a. The diaphragm pump 45 is configured such that the film body 451 is closely attached to the inner wall 453b, as shown in FIG. 13, when the positive pressure is supplied to the chamber portion 452f by the positive pressure source 62 connected to the flow port portion 452a. The volume of the chamber portion 453f partitioned by the film body 451 thereby becomes substantially zero, and thus the liquid in the chamber portion 453 flows out (pushed out) to the flow path 301 through the flow port portion 453a. The diaphragm pump 45 is configured such that the liquid amount that flows out in this case is about 6.0 ml. The high concentration reagent chamber 41, the RO water chamber 42, the diaphragm pump 45, the air pressure unit 6, the flow paths 300 to 304, and the electromagnetic valves 200 to 210 configure a constant amount liquid quantifying unit 50 (see FIG. 6) of the reagent preparing apparatus 4.

The conveyance chamber 46 (see FIG. 6) is arranged to store the reagent prepared in the mixing chambers 43 and 44. The conveyance chamber 46 is connected to the mixing chamber 43 through the electromagnetic valve 211, and is connected to the mixing chamber 44 through the electromagnetic valve 212. The conveyance chamber 46 is connected to the negative pressure source 61 through the electromagnetic valve 213 and connected to the positive pressure source 62 through the electromagnetic valve 214.

The supply chamber 47 is arranged to supply the prepared reagent to the measurement section 2. The supply chamber 47 is arranged with float switches 103 and 104 for detecting that the reagent stored in the chamber has reached the upper limit amount and the lower limit amount, respectively. The supply chamber 47 is also connected to the conveyance chamber 46 through the electromagnetic valve 215. The supply chamber 47 is connected to the measurement section 2 through the electromagnetic valve 216 and is able to discard the reagent in the chamber by opening the electromagnetic valve 217. The supply chamber 47 is configured to be opened to atmosphere at all times.

A conductivity sensor 400 for measuring the electrical conductivity of the reagent is arranged between the conveyance chamber 46 and the supply chamber 47. The conductivity sensor 400 includes a temperature sensor 401 for measuring the temperature of the reagent at the position arranged with the conductivity sensor 400.

The RO water producing unit 48 is configured to produce the RO water serving as the dilution liquid for diluting the high concentration reagent by using tap water. The RO water producing unit 48 includes a RO water reservoir tank 48a, a RO membrane 48b, and a filter 48c for protecting the RO membrane 48b by removing the impurities contained in the tap water. The RO water producing unit 48 also includes a high pressure pump 48d for applying high pressure to the water passing through the filter 48c so that water molecules pass through the RO membrane 48b, and an electromagnetic valve 218 for controlling the supply of tap water.

The RO water reservoir tank 48a is arranged to store the RO water passed through the RO membrane 48b. The RO water reservoir tank 48a is arranged with a float switch 105 for detecting that a predetermined amount of RO water is stored. The RO water reservoir tank 48a is also arranged with a conductivity sensor 402 for measuring the electrical conductivity of the RO water in the RO water reservoir tank 48a. The conductivity sensor 402 includes a temperature sensor 403 for measuring the temperature of the RO water.

Figure 14:
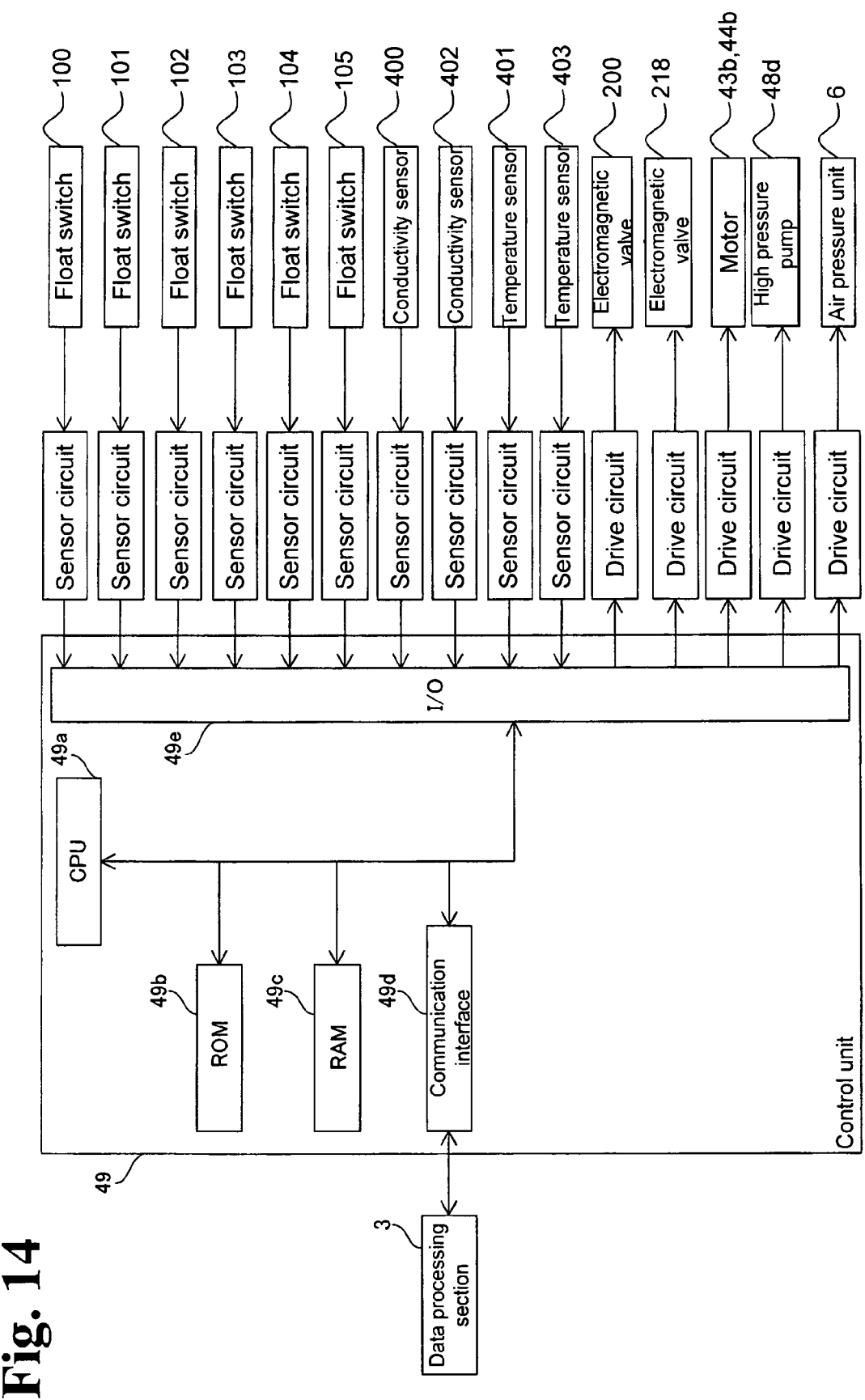
FIG. 14 is a block diagram describing a control unit of the reagent preparing apparatus according to one embodiment of the present invention.

As shown in FIG. 14, the control unit 49 includes a CPU 49a, a ROM 49b, a RAM 49c, a communication interface 49d connected to the data processing section 3, and an I/O (Input/Output) unit 49e connected to each unit of the reagent preparing apparatus 4 through each circuit.

The CPU 49a is arranged to execute the computer program stored in the ROM 49b and the computer program loaded in the RAM 49c. The CPU 49a uses the RAM 49c as a work region when executing the computer programs.

A general formula for obtaining the target value of the electrical conductivity of the reagent is shown in the following equation (1).

$$Z_0 = \{X + (A-1)Y\}/A \tag{1}$$

In equation (1), $Z_0$ is the target value (ms/cm) of the electrical conductivity at 25° C. of the reagent in which the high concentration reagent and the RO water are mixed and stirred, X is the electrical conductivity (ms/cm) at 25° C. of the high concentration reagent, Y is the electrical conductivity (ms/cm) at 25° C. of the RO water, and A is the dilution magnification (known) (25 times in the present embodiment). X is a value unique to the high concentration reagent, and is a known value obtained through experiment and the like in advance.

The correction equation for taking into consideration the temperature of the RO water obtained by the temperature sensor 403 and the temperature of the reagent obtained by the temperature sensor 401 is shown in the following equation (2).

$$Z = [\{X + (A-1)Y\}/A] \times \{1 + \alpha 1(T2-25)\} = [[X + (A-1)Y1/\{1 + \alpha 0(T1-25)\}]/A] \times \{1 + \alpha 1(T12-25)\} \tag{2}$$

In equation (2), Z is the target value (ms/cm) of the electrical conductivity at T2° C. of the reagent in which the high concentration reagent and the RO water are mixed and stirred, Y1 is the electrical conductivity (ms/cm) at T1° C. of the RO water, T1 is the temperature (° C.) of the RO water, T2 is the temperature (° C.) of the reagent in which the high concentration reagent and the RO water are mixed and stirred, 0 is the temperature coefficient with respect to 25° C. of the electrical conductivity of the RO water, and $\alpha 1$ is the temperature coefficient with respect to 25° C. of the electrical conductivity of the reagent in which the high concentration reagent and the RO water are mixed and stirred. The temperature coefficients $\alpha 0$ and $\alpha 1$ differ depending on the type and concentration of the liquid, but 0.02 is used for simplification in JIS (Japanese Industrial Standards).

In the present embodiment, the CPU 49a is configured to calculate the target value Z by equation (2). Therefore, the CPU 49a determines the target value based on the desired dilution magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent.

The communication interface 49d is configured to be able to transmit the error information generated in the reagent preparing apparatus 4 to the data processing section 3 so that the user can check the error that occurred in the reagent preparing apparatus 4. The error information may be information urging the replacement of the high concentration reagent tank 5, information notifying that the RO water is not being supplied, information notifying the abnormality of the negative pressure source 61 and the positive pressure source 62, and the like. The error notification is displayed on the display unit 32 of the data processing section 3 based on such error information.

As shown in FIG. 14, the I/O unit 49e is configured to be input with signals from the float switches 100 to 105, the conductivity sensors 400, 402 and the temperature sensors 401, 403 through each sensor circuit. The I/O unit 49e is configured to output the signal to each drive circuit for controlling the drive of the electromagnetic valves 200 to 218, the motors 43b, 44b, and the high pressure pump 48d through each drive circuit.

Figure 15:
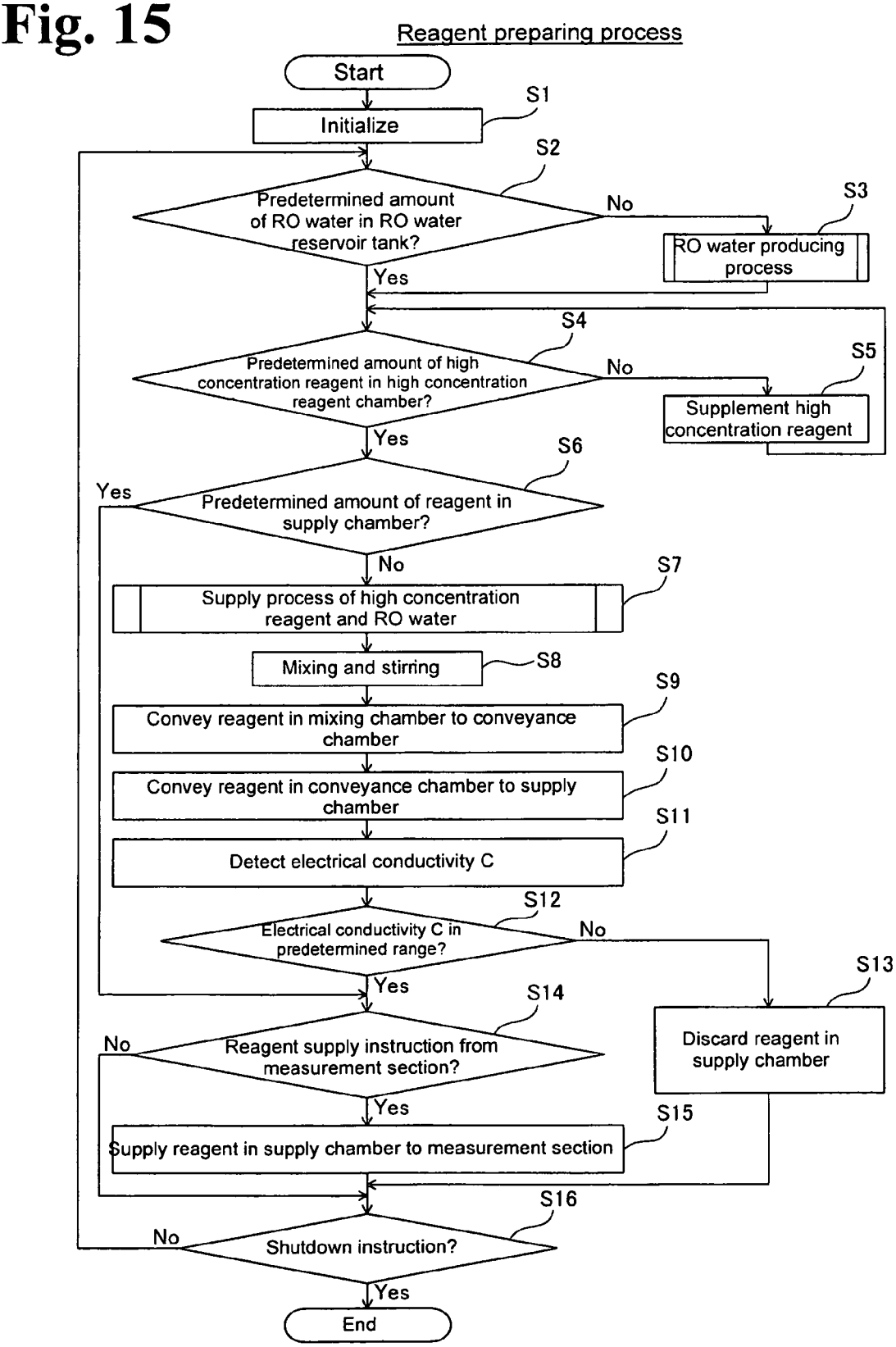
FIG. 15 is a flowchart describing the reagent preparing processing operation of the reagent preparing apparatus according to one embodiment of the present invention.

FIG. 15 is a flowchart describing the reagent preparing processing operation of the reagent preparing apparatus according to one embodiment shown in FIG. 1. The reagent preparing processing operation of the reagent preparing apparatus 4 according to one embodiment of the present invention will be described with reference to FIGS. 6 and 15.

First, in step S1 of FIG. 15, the CPU 49a initializes the computer program stored in the ROM 49b. In step S2, the CPU 49a judges whether or not a predetermined amount of RO water is stored in the RO water reservoir tank 48a shown in FIG. 6 based on the detection result of the float switch 105. If a predetermined amount of RO water is not stored in the RO water reservoir tank 48a, the RO water producing process is performed by the RO water producing unit 48 in step S3. The RO water is supplied from the RO water reservoir tank 48a to the RO water chamber 42 through the electromagnetic valve 205, and the CPU 49a closes the electromagnetic valve 205 and stops the supply of the RO water when the float switch 101 detects that the RO water has reached the upper limit amount.

Figure 16:
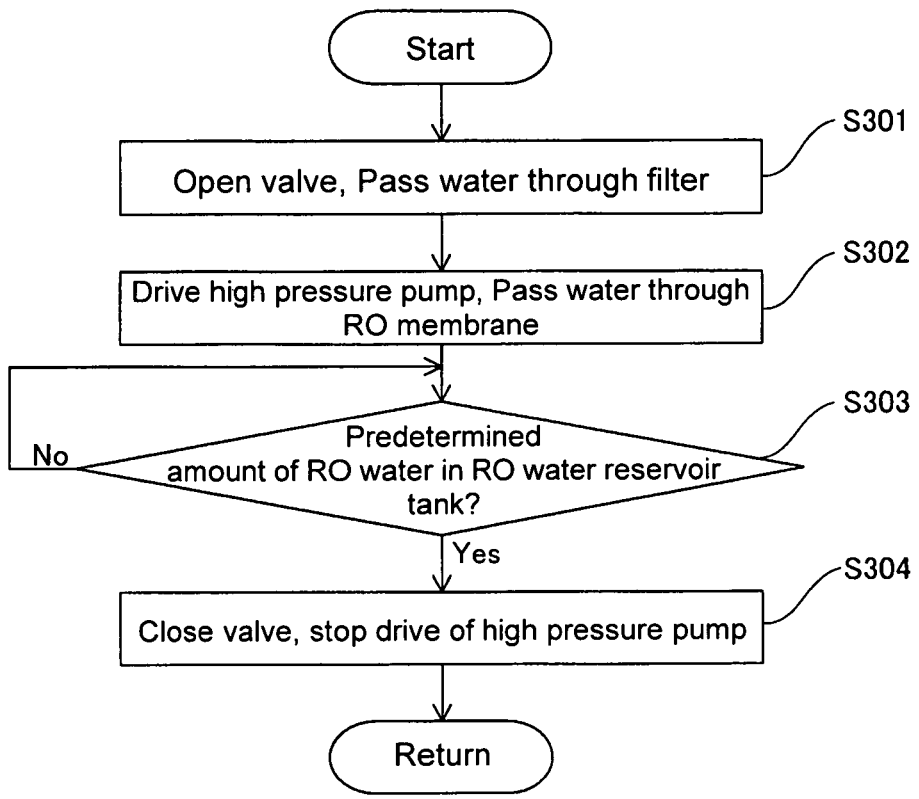
FIG. 16 is a flowchart describing the RO water producing processing operation in step S3 of the reagent preparing processing operation shown in FIG. 15.

FIG. 16 is a flowchart describing the RO water producing processing operation in step S3 of the reagent preparing processing operation shown in FIG. 15. The RO water producing processing operation in step S3 of the reagent preparing processing operation shown in FIG. 15 will be described with reference to FIGS. 6 and 16.

First, in step S301 of FIG. 16, the CPU 49a opens the electromagnetic valve 218 shown in FIG. 6, so that the tap water passes through the filter 48c. In step S302, the CPU 49a drives the high pressure pump 48d, so that the water passed through the filter 48c passes through the RO membrane 48b by high pressure. In step S303, whether or not a predetermined amount of RO water is stored in the RO water reservoir tank 48a is judged based on the detection result of the float switch 105. If the RO water does not satisfy a predetermined amount, such judgment is repeated and the RO water passed through the RO membrane 48b is continuously supplied to the RO water reservoir tank 48a. If the RO water reaches the predetermined amount, the electromagnetic valve 218 is closed, the drive of the high pressure pump 48d is stopped, and the operation is terminated in step S304.

If the predetermined amount of RO water is stored in the RO water reservoir tank 48a in the judgment of step S2 of FIG. 15, the CPU 49a judges whether or not a predetermined amount of high concentration reagent is stored in the high concentration reagent chamber 41 based on the detection result of the float switch 100 in step S4. If the predetermined amount of high concentration reagent is not stored, the high concentration reagent is supplemented from the high concentration reagent tank 5 to the high concentration reagent chamber 41 in step S5. Specifically, when the electromagnetic valves 200 and 201 are opened with the electromagnetic valves 202 and 203 closed, the high concentration reagent flows into the high concentration reagent chamber 41 by the negative pressure force.

If the predetermined amount of high concentration reagent is stored in the high concentration reagent chamber 41, the CPU 49a judges whether or not the predetermined amount of reagent is stored in the supply chamber 47 in step S6. If the predetermined amount of reagent is stored, the process proceeds to step S14. If the predetermined amount of reagent is not stored, the supply process of the high concentration reagent and the RO water is performed in step S7.

Figure 17:
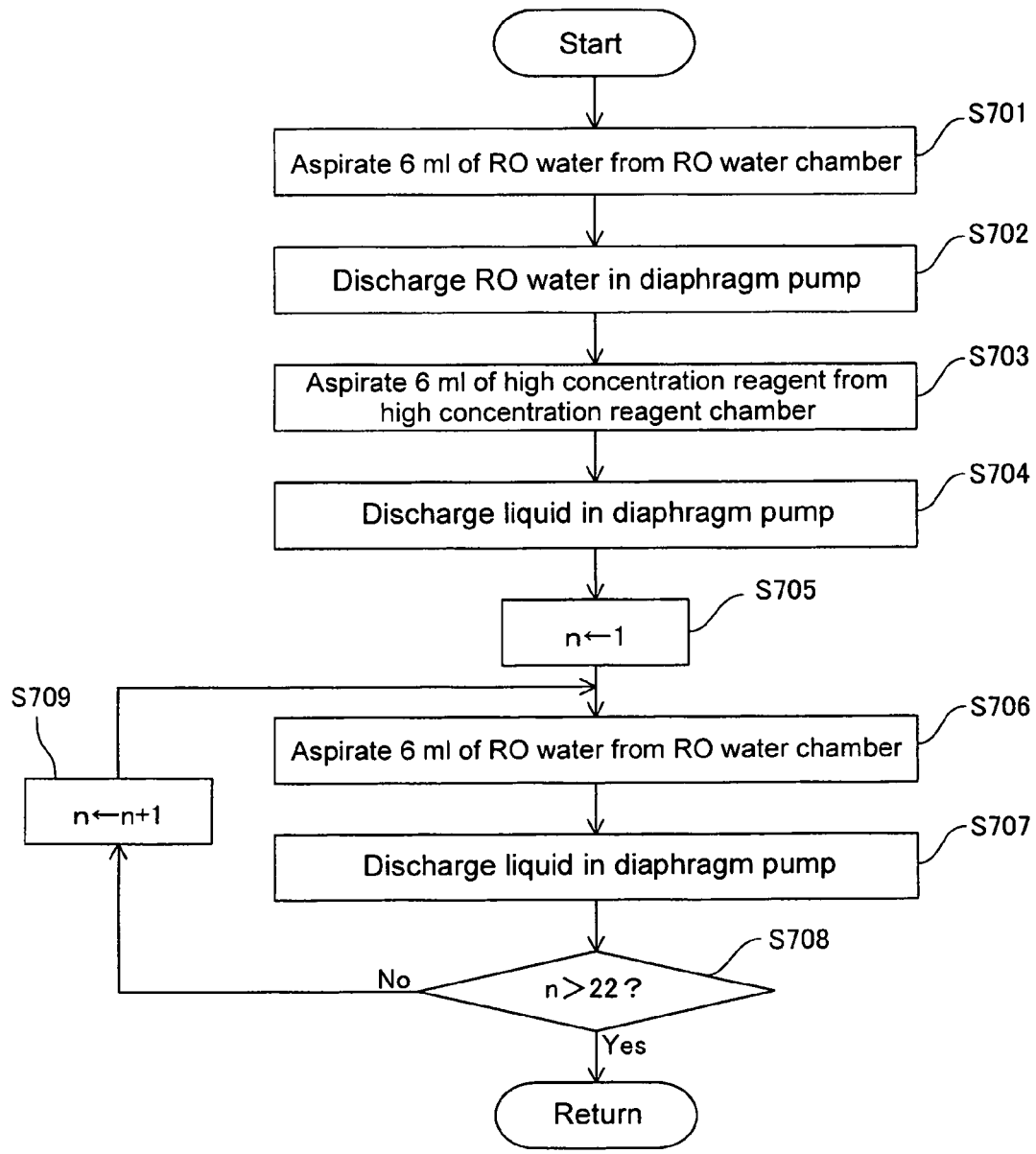
FIG. 17 is a flowchart describing the supply processing operation of the high concentration reagent and the RO water in step S7 of the reagent preparing processing operation shown in FIG. 15.

FIG. 17 is a flowchart describing the supply processing operation of the high concentration reagent and the RO water in step S7 of the reagent preparing processing operation shown in FIG. 15. The supply processing operation of the high concentration reagent and the RO water in step S7 of the reagent preparing processing operation shown in FIG. 15 will be described with reference to FIGS. 6, 12, 13, and 17.

First, the flow paths 301 to 304 shown in FIG. 6 are substantially filled with the RO water and the flow path 300 is substantially filled with the high concentration reagent in the initial state of the reagent preparing apparatus 4 (state immediately before the reagent preparing process). The flow path 300 and the flow path 301 are directly connected, but the high concentration reagent in the flow path 300 is less likely to be mixed with the RO water in the flow path 301 since the inner diameter of the flow path 300 (300a) is small or about 1.8 mm as opposed to the inner diameter of the flow path 301 of about 4.0 mm. The flow path 300a between the electromagnetic valve 203 and the flow path 301 is set such that the inner diameter is about 1.8 mm and the length is small or about 15 mm, and thus the amount of high concentration reagent in the flow path 300a is extremely small.

In step S701 of FIG. 17, about 6.0 ml of RO water is aspirated from the RO water chamber 42 by the diaphragm pump 45. Specifically, the negative pressure is supplied to the chamber portion 452f of the diaphragm pump 45, as shown in FIG. 12, by opening the electromagnetic valves 206 and 209, so that the RO water flows into the chamber portion 453f through the flow path 302. In step S702, the positive pressure is supplied to the chamber portion 452f, as shown in FIG. 13, by closing the electromagnetic valves 206 and 209, and then opening the electromagnetic valves 207 and 210, so that the RO water is discharged from the chamber portion 453f. Thus, about 6.0 ml of RO water is supplied to the mixing chamber 43 through the flow paths 301 and 303.

Thereafter, in step S703, about 6.0 ml of high concentration reagent is aspirated from the high concentration reagent chamber 41 by the diaphragm pump 45. Specifically, the negative pressure is supplied to the chamber portion 452f of the diaphragm pump 45, as shown in FIG. 12, by closing the electromagnetic valves 207 and 210, and then opening the electromagnetic valves 202, 203, and 209, so that the high concentration reagent is aspirated to the chamber portion 453f through the flow paths 300 and 301. In detail, about 6.0 ml of high concentration reagent flowed out from the high concentration reagent chamber 41 is mixed with the RO water remaining in the flow path 301, so that the mixed solution of the RO water and the high concentration reagent is aspirated to the chamber portion 453f. The flow path 301 in this case is filled with mixed solution of the RO water and the high concentration reagent. In other words, in this state, about 6.0 ml of high concentration reagent flowed out from the high concentration reagent chamber 41 exists in a region combining the chamber portion 453f and the flow path 301. The high concentration reagent also exists in the flow path 300a, but can be substantially ignored as the amount of high concentration reagent existing in the flow path 300a is very small, as described above. Furthermore, in aspirating the high concentration reagent after the reagent preparing processing operation of the second time, the high concentration reagent remaining in the flow path 300a by the reagent preparing processing operation of the previous time is pushed to the flow path 301 side, and thus about 6.0 ml of high concentration reagent more accurately exists in the region combining the chamber portion 453f and the flow path 301.

In step S704, the positive pressure is supplied to the chamber portion 452f, as shown in FIG. 13, by closing the electromagnetic valves 203 and 209, and then opening the electromagnetic valves 207 and 210, so that the mixed solution of the RO water and the high concentration reagent is discharged from the chamber portion 453f. The mixed solution of the RO water and the high concentration reagent is thereby supplied to the mixing chamber 43 through the flow paths 301 and 303. In this case, a few ml of high concentration reagent remains in the flow paths 301 and 303 in a state mixed with the RO water.

In step S705, the CPU 49a sets n=1. Here, n represents the discharging number of times of the RO water by the diaphragm pump 45, and is defined with an actual number starting from one. In step S706, about 6.0 ml of RO water is aspirated from the RO water chamber 42 by the diaphragm pump 45, similar to step S701. In step S707, the RO water is discharged from the chamber portion 453f of the diaphragm pump 45, similar to step S702. The high concentration reagent remaining in the flow paths 301 and 303 is thereby conveyed to the mixing chamber 43 with the RO water.

Thereafter, in step S708, the CPU 49a judges whether or not n is larger than 22. If n is not larger than 22, n=n+1 is set in step S709, and the operation of steps S706 to S709 are repeated until the n becomes larger than 22. In other words, with respect to the aspirating and discharging operation of the high concentration reagent of one time by the diaphragm pump 45, the operations of step S706 to step S709 are repeated until the aspirating and discharging operation of the RO water is carried out for 24 times. When n becomes larger than 22, the operation is terminated. Thus, about 6.0 ml×24 times=about 144 ml of RO water and about 6.0 ml×one time=about 6.0 ml of high concentration reagent are stored in the mixing chamber 43. After the aspirating and discharging operation of the high concentration reagent by the diaphragm pump 45, the high concentration reagent remaining in the flow paths 301 and 303 are all conveyed to the mixing chamber 43 as the aspirating and discharging operation of the RO water is performed for 23 times, and consequently, only the RO water remains in the flow paths 301 and 303.

In the above-described configuration, about 144 ml of RO water and about 6.0 ml of high concentration reagent can be conveyed to the mixing chamber 44 by driving the electromagnetic valve 208 in place of the electromagnetic valve 207.

After the supply process of the high concentration reagent and the RO water is performed in step S7 of FIG. 15, the high concentration reagent and the RO water stored in the mixing chamber 43 (44) is mixed and stirred by the stirring unit 43a (44a) in step S8. In step S9, the reagent in the mixing chamber 43 (44) is conveyed to the conveyance chamber 46 by opening the electromagnetic valves 211 (212) and 213 in step S9.

In step S10, the electromagnetic valves 211 (212) and 213 are closed, and then the electromagnetic valves 214 and 215 are opened, so that the reagent is conveyed from the conveyance chamber 46 to the supply chamber 47. In this case, the electrical conductivity C is measured by the conductivity sensor 400 and the temperature T2 of the reagent is measured by the temperature sensor 401 in step S11. In step S12, the CPU 49a judges whether or not the electrical conductivity C is within a predetermined range. Specifically, whether or not the measured electrical conductivity C is within the predetermined range is judged with respect to the target value Z of the electrical conductivity at the dilution magnification of 25 times calculated with equation (2). If the electrical conductivity C is not within the predetermined range, the electromagnetic valve 217 is opened and the reagent in the supply chamber 47 is discarded in step S13. Only the reagent diluted at satisfactory accuracy thus can be used by the measurement section.

In step S14, the CPU 49a judges whether or not a reagent supply instruction from the measurement section 2 transmitted through the data processing section 3 is made, where the process proceeds to step S16 if instruction is not made. If the reagent supply instruction is made, the electromagnetic valve 216 is opened and the reagent in the supply chamber 47 is supplied to the measurement section 2 in step S15. In step S16, the CPU 49a judges the presence of a shutdown instruction from the user, where the process proceeds to step S2 if the instruction is not made. If the shutdown instruction is made, the reagent preparing processing operation is terminated.

In the present embodiment, the diaphragm pump 45 used in common to hold a predetermined amount of high concentration reagent and RO water is arranged in the constant amount liquid quantifying unit 50, and the predetermined amount of high concentration reagent and RO water is supplied using the diaphragm pump 45, whereby the high concentration reagent can be diluted at satisfactory accuracy at the desired dilution magnification even if assembly error occurs in the diaphragm pump 45, because predetermined amount of both the high concentration reagent and the RO water can be held by the common diaphragm pump 45. As a complex reagent preparing operation does not need to be performed such as repeatedly supplying the RO water by a small amount at a time, the high concentration reagent can be diluted to the desired concentration at satisfactory accuracy with a simpler operation. Furthermore, the blood can be accurately analyzed with the blood analyzer 1 by using the reagent prepared at satisfactory accuracy to the desired concentration.

In the present embodiment, the CPU 49a controls the reagent preparing processing operation of the reagent preparing apparatus 4 such that the RO water is conveyed to the mixing chamber 43 (44) before the high concentration reagent is conveyed to the mixing chamber 43 (44) before preparing the reagent, so that the high concentration reagent can be conveyed to the mixing chamber 43 (44) storing the RO water. Thus, contamination of the mixing chamber 43 (44) by the high concentration reagent can be suppressed, and the high concentration reagent and the RO water can be efficiently mixed.

In the present embodiment, the CPU 49a controls the reagent preparing processing operation of the reagent preparing apparatus 4 such that the RO water is conveyed from the diaphragm pump 45 to the mixing chamber 43 (44) through the flow path 301 after the high concentration reagent is conveyed from the diaphragm pump 45 to the mixing chamber 43 (44) through the flow path 301 when preparing the reagent, so that the high concentration reagent remaining in the flow path 301 can be conveyed to the mixing chamber 43 (44) with the RO water to be subsequently conveyed. Thus, the high concentration reagent held by the diaphragm pump 45 is suppressed from remaining in the flow path 301. As a result, the high concentration reagent can be diluted to the desired concentration at satisfactory accuracy. Furthermore, since the high concentration reagent is suppressed from remaining in the flow path 301 after the high concentration reagent is diluted to the desired concentration, the high concentration reagent can be diluted at satisfactory accuracy even when diluting the high concentration reagent at the next time.

In the present embodiment, the reagent in which the concentration is not within a predetermined range (reagent in which the electrical conductivity C is not within a predetermined range) is prevented from being used as a reagent for processing the sample by arranging the conductivity sensor 400 for measuring the electrical conductivity C of the reagent stored in the reagent chamber 43 (44), the CPU 49a for determining whether or not the measurement value measured by the conductivity sensor 400 is within the predetermined range, and the electromagnetic valve 27 for discarding the reagent stored in the mixing chamber 43 (44) when the measurement value is not within the predetermined range.

In the present embodiment, the reagent can be prepared using two mixing chambers 43, 44 while switching the flow path 303 and the flow path 304 since the two mixing chambers 43, 44, and the electromagnetic valves 207, 208 for switching the flow path 303 for conveying the liquid to the mixing chamber 43 and the flow path 304 for conveying the liquid to the mixing chamber 44 are arranged. Greater amount of reagent thus can be rapidly prepared.

The embodiments disclosed here are illustrative in all aspects and should not be construed as being restrictive. The scope of the invention is defined by the Claims rather than by the embodiments described above, and all modifications equivalent in meaning and falling within the scope of the Claims are encompassed here.

For instance, the high concentration reagent is diluted to 25 times in the present embodiment, but the present invention is not limited thereto, and the high concentration reagent may be diluted to other magnifications other than 25 times such as 20 times. In this case, after conveying a predetermined amount of RO water to the mixing chamber 43 (44) once by using the diaphragm pump 45, the high concentration reagent is conveyed by predetermined amount to the mixing chamber 43 (44) for two times, and then the RO water is conveyed by predetermined amount to the mixing chamber 43 (44) for 37 times to prepare the reagent having dilution magnification of 20 times. When preparing the reagent having dilution magnification of 20 times by using the diaphragm pump 45, the RO water may be conveyed by predetermined amount to the mixing chamber 43 (44) once, then high concentration reagent may be conveyed by predetermined amount to the mixing chamber 43 (44) once, the RO water may be conveyed again by a predetermined amount once, the high concentration reagent may be conveyed by constant amount once, and then the RO water may be conveyed by predetermined amount for 36 times. The RO water and the high concentration reagent are thus alternately conveyed to the mixing chamber, and the RO water and the high concentration reagent can be more efficiently mixed in the mixing chamber.

In the present embodiment, an example in which the RO water serving as the dilution liquid is conveyed by predetermined amount to the mixing chamber once, and thereafter, the high concentration reagent is conveyed by predetermined amount once, and then the RO water is conveyed by predetermined amount for 23 times to prepare the reagent having dilution magnification of 25 times has been described, but the present invention is not limited thereto, and after the RO water is conveyed by predetermined amount for two times, the high concentration reagent may be conveyed by predetermined amount once and then the RO water may be conveyed by predetermined amount for 22 times to prepare the reagent having dilution function of 25 times.

In the above embodiment, an example in which the RO water serving as the dilution liquid is conveyed by predetermined amount to the mixing chamber once, and then the high concentration reagent is conveyed by predetermined amount once and the RO water is conveyed by predetermined amount for 23 times to prepare the reagent having dilution magnification of 25 times has been described, but the present invention is not limited thereto, and after the RO water is conveyed by predetermined amount once, the high concentration reagent is conveyed by predetermined amount for two times, and then the RO water is conveyed by predetermined amount for 47 times to prepare the reagent having dilution magnification of 25 times by using a diaphragm pump which capacity is half the diaphragm pump 45. The number of times the RO water and the high concentration reagent are conveyed to the mixing chamber can be increased, and thus the RO water and the high concentration reagent can be more efficiently mixed in the mixing chamber.

When preparing the reagent having dilution magnification of 25 times by using the diaphragm pump which capacity is half of the diaphragm pump 45, the RO water is conveyed by predetermined amount to the mixing chamber once, the high concentration reagent is conveyed by predetermined amount once, the RO water is again conveyed by predetermined amount once, the high concentration reagent is conveyed by predetermined amount once, and then the RO water is conveyed by predetermined amount for 46 times. The number of times the RO water and the high concentration reagent are conveyed to the mixing chamber can be increased, and furthermore, the RO water and the high concentration reagent can be alternately conveyed to the mixing chamber, and thus the RO water and the high concentration reagent can be more efficiently mixed.

In the above embodiment, the diaphragm pump has been described as an example of a constant amount holding instrument, but the present invention is not limited thereto, and may be a syringe pump in which the amount of stroke of the piston is fixed as long as it is a constant amount holding instrument capable of holding a predetermined amount of liquid in a single operation for holding liquid.

In the above embodiment, an example in which the conveyance chamber is arranged between the mixing chamber serving as the storage unit and the supply chamber has been described, but the present invention is not limited thereto, and the conveyance chamber may not be arranged between the mixing chamber and the supply chamber, and the mixing chamber may be used as the conveyance chamber.

Figure 18:
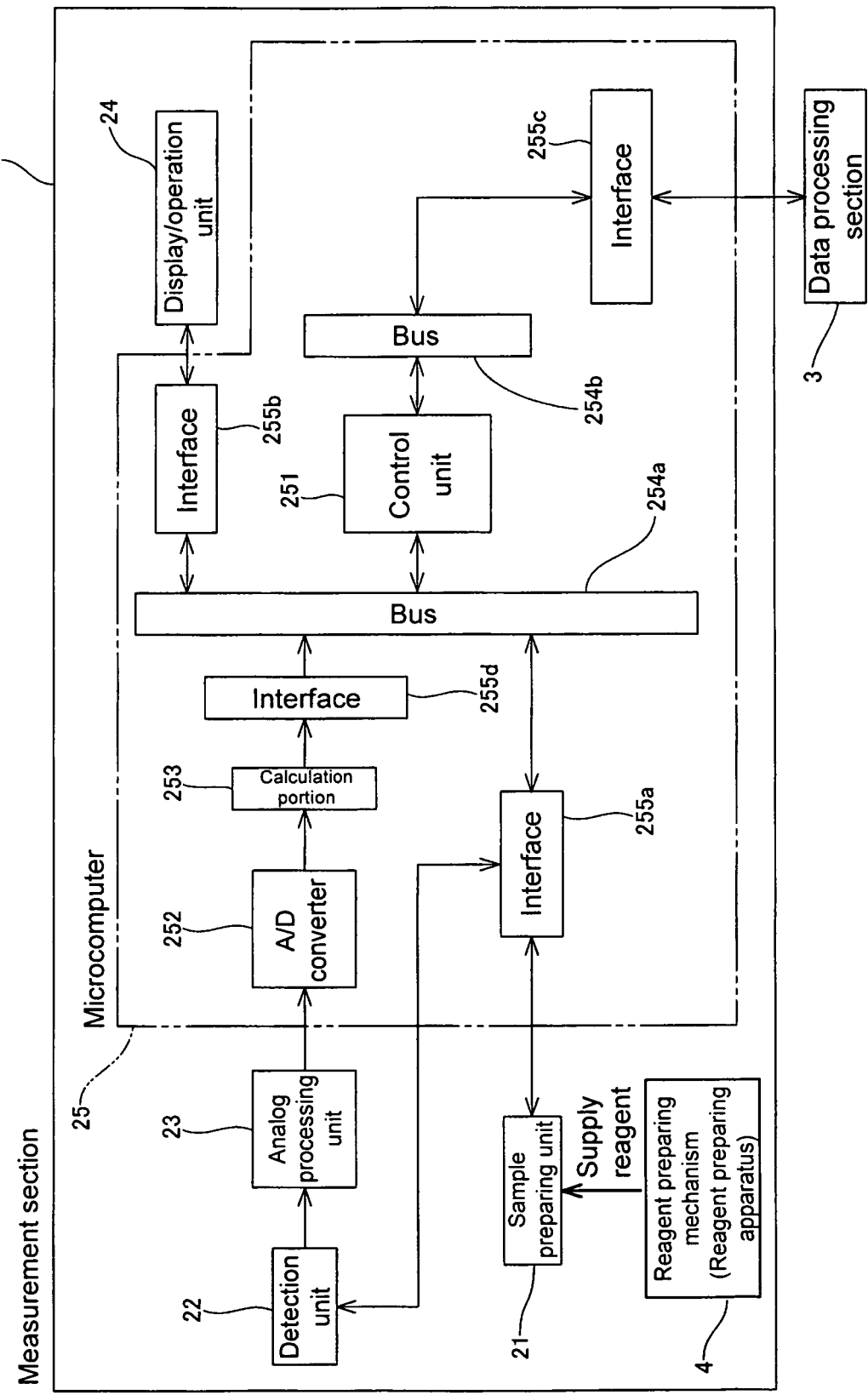
FIG. 18 is a block diagram describing a variant of the reagent preparing apparatus according to one embodiment shown in FIG. 1.

In the above embodiment, a reagent preparing apparatus installed separate from the measurement section has been described as an example of the reagent preparing apparatus, but the present invention is not limited thereto, and may be a reagent preparing apparatus arranged in the measurement section and functioning as a reagent preparing mechanism, as shown in FIG. 18. The measurement section (device) equipped with the reagent preparing mechanism includes a blood cell counting device, immunoassay device and smear producing device, but is particularly suited to the blood cell counting device in which the usage amount of the reagent is large.

In the above embodiment, an example of arranging one diaphragm pump serving as an example of the constant amount holding instrument has been described, but the present invention is not limited thereto, and two or more diaphragm pumps may be arranged. When preparing the reagent having desired dilution magnification by using two or more diaphragm pumps, the reagent of desired dilution magnification can be prepared in each diaphragm pump even if each diaphragm pump has assembly error and the like, and thus greater amount of reagent of desired dilution magnification can be prepared in a short period of time when the diaphragm pump is arranged in plurals.

In the above embodiment, an example of arranging a stirring unit in the mixing chamber serving as the storage unit, and mixing the high concentration reagent and the RO water in the mixing chamber has been described, but the present invention is not limited thereto, and the stirring unit may not be arranged in the mixing chamber, and the high concentration reagent and the RO water may be naturally mixed while being conveyed from the mixing chamber to the supply chamber through the conveyance chamber. In this case, the conductivity sensor serving as a physicality detection unit is preferably arranged immediately in front of the supply chamber.

In the above embodiment, an example where the conductivity sensor serving as the physicality detection unit is arranged between the conveyance chamber and the supply chamber has been described, but the present invention is not limited thereto, and may be arranged between the mixing chamber serving as a storage unit and the conveyance chamber. In this case, the reagent which electrical conductivity C is not within a predetermined range may be discarded from the conveyance chamber.

In the above embodiment, the conductivity sensor for measuring the electrical conductivity has been described as an example of the physicality detection unit, but the present invention is not limited thereto, and a pH sensor for measuring the pH of the reagent may be arranged. In this case, whether or not to discard the reagent may be judged based on the measurement result of the pH.

In the above embodiment, the control process of the constant amount of liquid conveying operation by the diaphragm pump, the determination process on whether or not the electrical conductivity of the reagent is within a predetermined range, the control process of the discarding operation of the reagent in the supply chamber, and the like may be executed by one CPU 49a, but the present invention is not limited thereto, and such processes may be executed by a plurality of CPUs. Such processes may be executed by a CPU arranged exterior to the reagent preparing apparatus such as a CPU arranged in the measurement section or a CPU arranged in the data processing section.

In the above embodiment, the diluted solution is prepared by diluting the salt solution of high salinity that acts as the undiluted solution of the diluted solution, but the present invention is not limited thereto, and the hemolyzing agent and the staining fluid may be prepared by diluting the solution or the undiluted solution of the hemolyzing agent and the staining fluid or the reagent may be prepared by diluting the undiluted solution of other reagents.

In the above embodiment, the reagent is prepared by diluting the high concentration reagent with the RO water, but the present invention is not limited thereto, and the reagent may be prepared by diluting the high concentration reagent with distilled water or pure water. The reagent may be prepared from liquid such as methanol or ether, which is liquid other than water, and the high concentration reagent depending on the type of high concentration reagent.

What is claimed is:

1. A reagent preparing apparatus for preparing a reagent for processing a sample, by using a first liquid and a second liquid, comprising:
    a first liquid chamber for containing a first liquid;
    a second liquid chamber for containing a second liquid;
    a storage unit for mixing the first liquid and the second liquid;
    a constant amount liquid quantifying unit comprising:
        a constant amount holding instrument in fluid communication with the first liquid chamber, the second liquid chamber, and the storage unit, wherein the constant amount holding instrument is configured to transfer a constant amount of liquid from each of the first and second liquid chambers to the storage unit, and
        a first transfer flow path for transferring liquid from the constant amount holding instrument to the storage unit, wherein the first liquid chamber and the second liquid chamber are connected to the first transfer flow path between the constant amount holding instrument and the storage unit; and
    a controller configured to control the constant amount liquid quantifying unit so as to supply a first amount of the first liquid from the first liquid chamber to the storage unit by using the constant amount holding instrument and configured to control the constant amount liquid quantifying unit so as to supply a second amount of the second liquid from the second liquid chamber to the storage unit by using the constant amount holding instrument, so that a reagent is prepared from the first amount of the first liquid and the second amount of the second liquid in the storage unit.

2. The reagent preparing apparatus of claim 1, wherein
    the first liquid chamber contains the first liquid,
    the second liquid chamber contains the second liquid,
    the first liquid is an undiluted solution of the reagent and
    the second liquid is a dilution liquid for diluting the undiluted solution of the reagent.

3. The reagent preparing apparatus of claim 1, wherein the constant amount holding instrument is configured to transfer the constant amount of liquid in a single operation, the single operation comprising:
    consecutively aspirating the constant amount of the first liquid from the first liquid chamber and discharging the constant amount of the first liquid to the storage unit by the constant amount holding instrument, or
    consecutively aspirating the constant amount of the second liquid from the second liquid chamber and discharging the constant amount of the second liquid to the storage unit by the constant amount holding instrument.

4. The reagent preparing apparatus of claim 1, further comprising an air pressure unit, wherein
    the constant amount holding instrument is a diaphragm pump; and
    the constant amount liquid quantifying unit drives the diaphragm pump by air pressure supplied from the air pressure unit.

5. The reagent preparing apparatus of claim 1, wherein the first amount is a product of a first number times the constant amount and the second amount is a product of a second number times the constant amount.

6. The reagent preparing apparatus of claim 5, wherein
    the controller controls the constant amount liquid quantifying unit so as to transfer the first amount of the first liquid to the storage unit by transferring the constant amount of the first liquid for the first number of times and to transfer the second amount of the second liquid to the storage unit by transferring the constant amount of the second liquid for the second number of times, and
    the first number is different from the second number.

7. The reagent preparing apparatus of claim 1, wherein
    the controller controls the constant amount liquid quantifying unit so as to transfer the second liquid to the storage unit before transferring the first liquid to the storage unit when preparing the reagent.

8. The reagent preparing apparatus of claim 1, wherein
    the controller controls the constant amount liquid quantifying unit so as to transfer the second liquid to the storage unit after transferring the first liquid to the storage unit when preparing the reagent.

9. The reagent preparing apparatus of claim 1, wherein the constant amount liquid quantifying unit comprises:
    a second transfer flow path, connected to the first transfer flow path, for transferring the second liquid to the constant amount holding instrument through a portion of the first transfer flow path; and
a valve, arranged in the vicinity of the first transfer flow path on the second transfer flow path, for supplying the second liquid to the first transfer flow path.

10. The reagent preparing apparatus of claim 1, wherein the constant amount liquid quantifying unit comprises:
a second transfer flow path, connected to the first transfer flow path, for transferring the first liquid to the constant amount holding instrument through a portion of the first transfer flow path; and
a valve, arranged in the vicinity of the first transfer flow path on the second transfer flow path, for supplying the first liquid to the first transfer flow path.

11. The reagent preparing apparatus of claim 1, wherein the storage unit is a first storage unit, further comprising a second storage unit for storing the first liquid and the second liquid transferred by the constant amount liquid quantifying unit, wherein
the constant amount liquid quantifying unit comprises:
a second transfer flow path for transferring liquid from the constant amount holding instrument to the second storage unit; and
a flow path switching unit for switching a flow path of liquid between the first transfer flow path and the second transfer flow path so that the liquid in the constant amount holding instrument is transferred to the first storage unit or the second storage unit.

12. The reagent preparing apparatus of claim 11, wherein the first transfer path comprises a common flow path used in common with the second transfer flow path in a zone from the constant amount holding instrument to a predetermined switching position, and a first dedicated flow path for connecting the predetermined switching position and the first storage unit; and
the second transfer flow path comprises the common flow path and a second dedicated flow path for connecting the predetermined switching position and the second storage unit.

13. The reagent preparing apparatus of claim 1, further comprising:
a physicality detector for detecting a value indicating a physicality related to a concentration of a reagent prepared from the first liquid and the second liquid stored in the storage unit;
a physicality determiner for determining whether or not a detection value detected by the physicality detector is within a predetermined range; and
a discarding unit for discarding the reagent stored in the storage unit when determined by the physicality determiner that the detection value is not within the predetermined value.

14. The reagent preparing apparatus of claim 1, further comprising:
a supply instruction receiver for accepting a supply instruction for supplying a reagent prepared from the first liquid and the second liquid; and
a reagent supply unit for supplying the prepared reagent to a sample processing apparatus for processing a sample by using the prepared reagent, when the supply instruction receiver has accepted the supply instruction.

15. The reagent preparing apparatus of claim 1, further comprising:
a reagent storing unit for storing a reagent prepared from the first liquid and the second liquid, the reagent storing unit being in fluid communication with the storage unit;
a reagent amount detector for detecting a reagent amount stored in the reagent storing unit; and
a reagent amount determiner for determining whether or not a predetermined amount of the reagent is being stored in the reagent storing unit, based on a detection result detected by the reagent amount detector,
wherein the controller controls the constant amount liquid quantifying unit so as to start an operation of transferring the first liquid and the second liquid to the storage unit when determined that the predetermined amount of the reagent is not being stored in the reagent storing unit by the reagent amount determiner.

16. The reagent preparing apparatus of claim 1, wherein the reagent preparing apparatus further comprises a second liquid producing unit for producing the second liquid and supplying the second liquid to the second liquid chamber, wherein the second liquid chamber is in fluid communication with the second liquid producing unit.

17. A sample processing apparatus comprising:
a reagent preparing unit for preparing a reagent by using a first liquid and a second liquid, the reagent preparing unit comprising:
a first liquid chamber for containing a first liquid;
a second liquid chamber for containing a second liquid;
a storage unit for mixing the first liquid and the second liquid;
a constant amount liquid quantifying unit comprising:
a constant amount holding instrument in fluid communication with the first liquid chamber, the second liquid chamber, and the storage unit, wherein the constant amount holding instrument is configured to transfer a constant amount of liquid from each of the first and second liquid chambers to the storage unit, and
a first transfer flow path for transferring liquid from the constant amount holding instrument to the storage unit, wherein the first liquid chamber and the second liquid chamber are connected to the first transfer flow path between the constant amount holding instrument and the storage unit; and a controller configured to control the constant amount liquid quantifying unit so as to supply a first amount of the first liquid from the first liquid chamber to the storage unit by using the constant amount holding instrument and configured to control the constant amount liquid quantifying unit so as to supply a second amount of the second liquid from the second liquid chamber to the storage unit by using the constant amount holding instrument, so that a reagent is prepared from the first amount of the first liquid and the second amount of the second liquid in the storage unit; and
a sample processing unit in fluid communication with the constant amount liquid quantifying unit, the sample processing unit configured to prepare a measurement sample from a blood sample and the reagent supplied from the reagent preparing unit and to detect blood cells in the measurement sample.

18. The sample processing apparatus of claim 17, wherein the first liquid is an undiluted solution of the reagent,
the second liquid is a dilution liquid for diluting the undiluted solution of the reagent, and
the first amount is a product of a first number times the constant amount and the second amount is a product of a second number times the constant amount.

19. The sample processing apparatus of claim 17, wherein the controller controls the constant amount liquid quantifying unit so as to transfer the first amount of the first liquid to the storage unit by transferring the constant amount of the first liquid for the first number of times and to transfer the second amount of the second liquid to the storage unit by transferring the constant amount of the second liquid for the second number of times, and the first number is different from the second number.

* * * * *